(12) United States Patent
Ahrens et al.

(10) Patent No.: US 9,352,057 B2
(45) Date of Patent: May 31, 2016

(54) COMPOSITIONS AND METHODS FOR PRODUCING EMULSIONS FOR NUCLEAR MAGNETIC RESONANCE TECHNIQUES AND OTHER APPLICATIONS

(71) Applicant: Celsense, Inc., Pittsburgh, PA (US)

(72) Inventors: Eric T. Ahrens, Pittsburgh, PA (US); Jelena Janjic, Pittsburgh, PA (US)

(73) Assignee: Celsense, Inc., Pittsburgh, PA (US)

( * ) Notice: Subject to any disclaimer, the term of this patent is extended or adjusted under 35 U.S.C. 154(b) by 178 days.

(21) Appl. No.: 13/901,663

(22) Filed: May 24, 2013

(65) Prior Publication Data

US 2013/0343999 A1  Dec. 26, 2013

Related U.S. Application Data

(63) Continuation of application No. 12/990,533, filed as application No. PCT/US2009/002706 on May 1, 2009, now abandoned.

(60) Provisional application No. 61/126,305, filed on May 2, 2008, provisional application No. 61/132,420, filed on Jun. 17, 2008.

(51) Int. Cl.
| | |
|---|---|
| A61K 49/10 | (2006.01) |
| A61K 49/00 | (2006.01) |
| A61K 49/18 | (2006.01) |

(52) U.S. Cl.
CPC .............. *A61K 49/10* (2013.01); *A61K 49/0002* (2013.01); *A61K 49/0078* (2013.01); *A61K 49/1806* (2013.01); *A61K 49/1812* (2013.01); *A61K 49/1896* (2013.01)

(58) Field of Classification Search
CPC ........... A61K 49/0002; A61K 49/0078; A61K 49/10; A61K 49/1806; A61K 49/1812; A61K 49/896
See application file for complete search history.

(56) References Cited

U.S. PATENT DOCUMENTS

| | | | |
|---|---|---|---|
| 6,193,952 B1 * | 2/2001 | Kabalnov et al. ............ | 424/9.52 |
| 6,461,586 B1 | 10/2002 | Unger | |
| 2002/0102216 A1 * | 8/2002 | Lanza et al. ................. | 424/9.52 |
| 2004/0146462 A1 * | 7/2004 | Eriksen et al. ............... | 424/9.51 |
| 2006/0239919 A1 * | 10/2006 | Wickline et al. .............. | 424/9.3 |

FOREIGN PATENT DOCUMENTS

| | | |
|---|---|---|
| WO | 2005/072780 | 8/2005 |
| WO | 2006/096499 | 9/2006 |

OTHER PUBLICATIONS

Fan et al (2006) "MRI of perfluorocarbon emulsion kinetics in rodent mammary tumours". Physics in Medicine and Biology., 51: 211-220.*
Notification of Transmittal of the International Search Report and the Written Opinion of the International Searching Authority, or the Declaration, PCT U.S. Appl. No. PCT/US2009/002706, Sep. 12, 2009.
Morawski, Anne M., et al., "Quantitative 'Magnetic Resonance Immunohistochemistry' with Ligand-Targeted 19F Nanoparticles", Magnetic Resonance in Medicine, Dec. 1, 2004, pp. 1255-1262, vol. 52, No. 6, Academic Press, Duluth, MN.
Ahrens, Eric T., et al., "In vivo imaging platform for tracking immunotherapeutic cells", Nature Biotechnologey, Aug. 1, 2005, pp. 983-987, vol. 23, No. 8, Nature Publishing Group, New York, NY.
Partlow, Kathryn C., et al., "F magnetic resonance imaging for stem/progenitor cell tracking with multiple unique perfluorocarbon nanobeacons", The FASEB Journal, Jun. 2007, pp. 1647-1654, vol. 21, No. 8.
McNab, J.A., et al., "Tissue oxygen tension measurements in the Shionogi model of prostate cancer using 19F MRS and MRI", Magnetic Resonance Materials in Physics, Biology and Medicine, Dec. 1, 2004, pp. 288-295, vol. 17, No. 3-6, Chapman and Hall, London, Great Britain.
International Preliminary Report on Patentability, PCT U.S. Appl. No. PCT/US2009/002706, Nov. 11, 2010.
Invitation to Pay Additional Fees and, where Applicable, Protest Fee, PCT U.S. Appl. No. PCT/US2009/002706, Apr. 9, 2009.
Patent Examination Report No. 1, Australian Serial No. 2009241762, Oct. 17, 2013.
Official Action (English translation), Japanese Serial No. 2011-507466, Oct. 9, 2013.
Communication pursuant to Article 94(3) EPC, European Serial No. 09739238.5, Jul. 22, 2011.

* cited by examiner

*Primary Examiner* — Anoop Singh
*Assistant Examiner* — Doan Phan
(74) *Attorney, Agent, or Firm* — Beck & Thomas, P.C.

(57) ABSTRACT

The disclosure provides, in part, compositions and methods for producing emulsions. In certain embodiments, emulsions of the disclosure can be used for the detection of inflammation and cell tracking using MRI. The disclosure provides, in part, methods for labeling, detecting and quantifying cell members, in vivo. In certain embodiments, emulsions can be used as an artificial blood substitute.

4 Claims, 10 Drawing Sheets

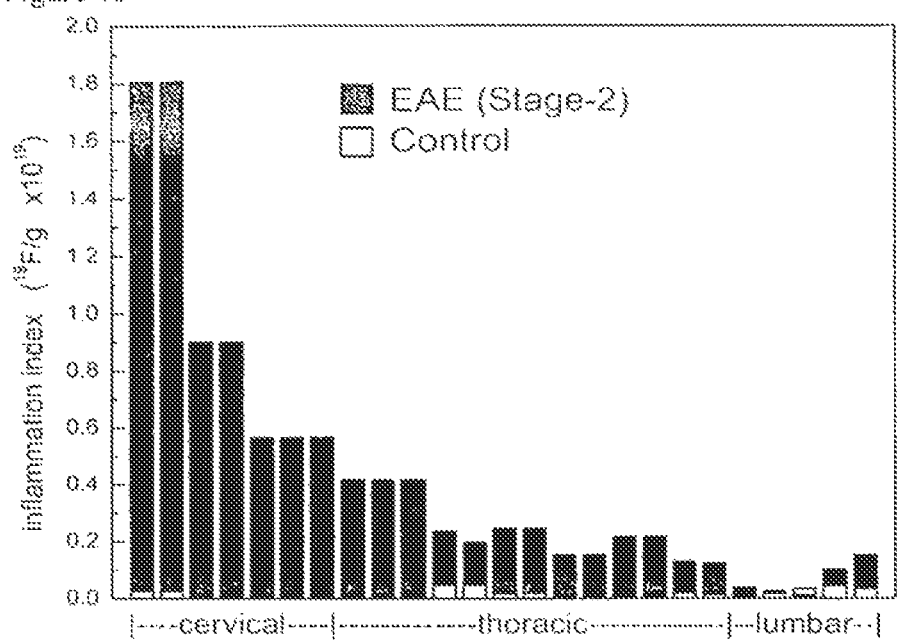

COMPOSITIONS AND METHODS FOR PRODUCING EMULSIONS FOR NUCLEAR MAGNETIC RESONANCE TECHNIQUES AND OTHER APPLICATIONS

This application is a continuation of U.S. application Ser. No. 12/990,533 filed Jan. 18, 2011, now abandoned, which in turn claimed priority as a national stage entry of PCT Application No. PCT/US09/002706 filed May 1, 2009, which in turn claimed priority to and the benefit of the filing date of U.S. Provisional Patent Applications Nos. 61/126,305, filed May 2, 2008, and 61/132,420, filed Jun. 17, 2008.

RELATED APPLICATIONS

This application claims the benefit of the filing date of U.S. Provisional Patent Applications 61/126,305, filed May 2, 2008 and 61/132,420, filed Jun. 17, 2008. The entire teachings of these application are incorporated by reference herein.

BACKGROUND

Many biological processes are carried out by populations of cells. For example, cells of the immune system are recruited from the bloodstream to areas of inflammation or infection, resulting in an accumulation of immune cells at the affected site. A marked infiltration of immune cells often occurs in tissues affected by autoimmune diseases, cancers and infection. Likewise, transplant rejection is mediated by host immune cells that enter and destroy the transplanted tissue. There is also growing evidence that stem cells originating in the bone marrow migrate through the bloodstream and assist in the regeneration of damaged tissues.

Furthermore, the most immediately promising area of biologic therapy involves the emerging field of cellular therapy. Cellular therapy is broadly defined as the treatment of human disease by the administration of therapeutic rolls that have been selected, multiplied, and pharmacologically treated outside the body, or ex vivo. These cells may be derived from the patient (autologous cells), from another human (allogenic cells), from other organisms (xenogenic cells), or from immortalized cell lines.

Cells represent the ultimate therapeutic system because of their ability to carry out complex functions and their responsiveness to changes in the surrounding tissue or host organism. In the simplest mode of cellular therapy, cells can be isolated, grown in quantity ex vivo, and implanted in patients to produce and secrete soluble factors that directly address the mechanism of disease. Cells can also accomplish tasks as complex as reconstitution of tissues, organs, or immune responses based on their ability to home to specific sites within the body, to exit from circulation, and to integrate into specific tissue or differentiate into new tissue. Other cellular therapeutics can be programmed for tumor killing or treating metastases (e.g., immunotherapeutics).

Although dynamic cell populations play a key role in significant diseases, present technologies for monitoring the location and movement of cells in vivo are quite limited. Typically, cell movements are monitored only in "snap shots" obtained by histological analysis of tissue biopsies. However, the process of sampling a tissue often alters the behavior of cells, and only a limited number of biopsies can be obtained from a particular tissue or organ. Some progress has been made studying cell movements via in vitro assays and isolated tissues ex-vivo. Existing instruments for non-invasive analysis of living organisms are, at present, ill-suited for tracking living cells. Light-based imaging technologies, such as bioluminescence (e.g. luciferases) technologies, are often ineffective at visualizing deep structures because most mammalian tissues are optically opaque. Positron emission tomography (PET) techniques using radioactively-labeled probes are highly sensitive. However, PET instrumentation is often limited to a resolution of several millimeters and is unable to resolve fine details of tissues and organs. Furthermore, labeled cells cannot be detected for time periods that extend beyond a typical PET radioisotope half-life, and generally PET is not useful for longitudinal studies. In order to gain a fundamental understanding of cellular processes, new ways to visualize and quantify the population dynamics of specific cell types in vivo must be developed.

Magnetic resonance imaging (MRI) is a widely used clinical diagnostic tool because it is non-invasive, allows views into optically opaque subjects, and provides contrast among soft tissues at reasonably high spatial resolution. Conventional MRI focuses almost exclusively on visualizing anatomy and has no specificity for any particular cell type, The 'probe' used by conventional MRI is the ubiquitous proton ($^1$H) in mobile water molecules. New classes of exogenous MRI probes or reagents are needed to facilitate cell-specific imaging in living subjects.

SUMMARY

In certain aspects, the application discloses an aqueous composition comprising perfluoro-15-crown-5 ether or PFPE oxide, an emulsifier, a surfactant co-mixture, and an additive. In certain embodiments, the surfactant co-mixture comprises 70 mol % lecithin, 28 mol % cholesterol, and 2 mol % DPPE. In certain embodiments, the additive is propylene glycol. In certain embodiments, the emulsifier is also a non-ionic solubiliser. In certain embodiments, the emulsifier comprises glycerol polyethylene glycol ricinoleate.

In certain embodiments, the composition comprises perfluor-15-crown-5 ether or PFPE oxide in the range of 20% to 50% w/v. In certain embodiments, the composition comprises perfluor-15-crown-5 ether or PFPE oxide in the range of 25% to 35% w/v. In certain embodiments, the composition comprises perfluor-15-crown-5 ether or PFPE oxide in the range of 30% to 40% w/v. In certain embodiments, the composition comprises perfluor-15-crown-5 ether or PFPE oxide in the range of 35% to 36% w/v. In certain embodiments, the composition comprises perfluor-15-crown-5 ether or PFPE oxide in 35.6% w/v.

In certain embodiments, the composition comprises the emulsifier in the range of 1 % to 10% w/v. In certain embodiments, the composition comprises the emulsifier in the range of 1% to 5% w/v. In certain embodiments, the composition comprises the emulsifier in 3% w/v.

In certain embodiments, the composition comprises propylene glycol in the range of 1% to 10% w/v. In certain embodiments, the composition comprises propylene glycol in the range of 1% to 5% w/v. In certain embodiments, the composition comprises propylene glycol, in 2% w/v. In certain embodiments, the composition comprises the surfactant co-mixture comprising lecithin, cholesterol, and DPPE in the range of 1% to 10% w/v. In certain embodiments, the composition comprises the surfactant co-mixture comprising lecithin, cholesterol, and DPPE in the range of 1% to 5% w/v. In certain embodiments, the composition comprises the surfactant co-mixture comprising lecithin, cholesterol, and DPPE in 2% w/v.

In certain aspects, the application discloses an aqueous composition comprising perfluoro-15-crown-5 ether or PFPE oxide in 35.6% w/v, an emulsifier in 3.0% w/v, a surfactant co-mixture in 2.0% w/v, wherein the surfactant co-mixture comprises lecithin, cholesterol, and DPPE, and an additive in 2.0% w/v, wherein the additive is propylene glycol. In certain embodiments, the emulsifier is also a non-ionic solubiliser. In certain embodiments, the emulsifier comprises glycerol polyethylene-glycol ricinoleate.

In certain aspects, the application discloses an aqueous composition comprising perfluoro-15-crown-5 ether or PFPE oxide and a block copolymer, wherein the composition comprises perfluoro-15-crown-5 ether or PFPE oxide in the range of 10% to 20% w/w, and wherein the composition comprises the block copolymer in the range of 0.1% to 2.0% w/w. In certain embodiments, the block copolymer is a tri-block copolymer which comprises polyethyleneoxide and polypropylenoxide. In certain such embodiments, the block copolymer is poly(ethylene oxide)-poly(propylene oxide)-poly(ethylene oxide) (PEO-PPO-PEO) tri-block copolymer comprising 80% PEO content.

In certain embodiments, the composition comprises perfluoro-15-crown-5 ether or PFPE oxide in the range of 12% to 17% w/w. In certain embodiments, the composition comprises perfluoro-15-crown-5 ether or PFPE oxide in 15% w/w. In certain embodiments, the composition comprises the block copolymer in the range of 0.1% to 1.0% w/w. In certain embodiments, the composition comprises the block copolymer in 0.6% w/w.

In certain aspects, the application discloses an aqueous composition comprising perfluoro-15-crown-5 ether or PFPE oxide in 15% w/w and a block copolymer in 0.6% w/w. In certain embodiments, the block copolymer is a tri-block copolymer which comprises polyemthyleneoxide and polypropyleneoxide. In certain such embodiments, the block copolymer is polyethylene oxide)-polypropylene oxide)-poly(ethyl oxide) (PEO-PPO-PEO) tri-block copolymer comprising 80% PEO content.

In certain embodiments, the composition further comprises protamine sulfate in the range of 0.01% to 1.0% w/w. In certain embodiments, the composition comprises protamine sulfate in the range of 0.01% to 0.5% w/w. In certain embodiments, the composition comprises protamine sulfate in the range of 0.01% to 0.1% w/w. In certain embodiments, the composition comprises protamine sulfate in 0.04% w/w.

In certain aspects, the application discloses an emulsion comprising a composition of any one of the embodiments described herein. In certain embodiments, the emulsion has a mean droplet size of less than 200 nM in diameter. In certain embodiments, the emulsion is stable at temperatures ranging from 4° C. to 37° C. In certain embodiments, the emulsion has a polydispersity index ranging from 0.1 to 0.2.

In certain aspects, the application discloses a method for preparing an emulsion of the application comprising high energy methods. In certain embodiments, the high energy method is microfluidization. In certain embodiments, the high energy method is sonication.

In certain aspects, the application discloses a method for labeling a cell, the method comprising contacting the cell ex vivo with an emulsion of the application under conditions such that the fluorocarbon imaging reagent becomes associated with the cell.

In certain aspects, the application discloses a method for detecting a cell in a subject, the method comprising: a) administering to the subject a cell that is labeled with an emulsion of the application; and b) examining at least a portion of the subject by a nuclear magnetic resonance technique, thereby detecting a labeled cell in the subject.

In certain aspects, the application discloses a method for detecting transplanted cells in a transplant recipient, the method comprising: a) administering cells for transplant to a transplant recipient, at least a portion of which cells for transplant are labeled with an emulsion of the application; b) examining at least a portion of the subject by a nuclear magnetic resonance technique, thereby detecting the labeled cells.

In certain aspects, the application discloses a method for quantifying cell number in vivo, the method comprising: a) administering to the subject cells that are labeled with an emulsion of the application; b) examining at least a portion of the subject by a nuclear magnetic resonance technique, thereby detecting labeled cells in the subject; and c) quantifying the number of labeled cells in a region of interest (ROI).

In certain aspects, the application discloses a method for quantifying leukocyte number in vivo, the method comprising: a) administering to the subject an emulsion of the application; b) extravesating a sample of peripheral blood from the subject and measure the effective cell loading of leukocytes; c) examining at least a portion of the subject by a nuclear magnetic resonance technique, thereby detecting labeled cells in the subject; and d) quantifying the number of labeled cells in a region of interest (ROI). In certain embodiments, population of cells are sorted out of the sample prior to the measuring cell loading and the proportion of said cells is used to quantify the number of labeled cells in that population in a ROI.

In certain aspects, the application discloses a method for labeling a cell, the method comprising contacting the cell in vivo with an emulsion of the application under conditions such that the fluorocarbon imaging reagent becomes associated with the cell.

In certain aspects, the application discloses a method for detecting a cell in a subject, the method comprising: a) administering to the subject an emulsion of the application; and b) examining at least a portion of the subject by a nuclear magnetic resonance technique, thereby detecting a labeled cell in the subject.

In certain aspects, the application discloses a method for measuring the partial pressure of oxygen in a tissue, the method comprising contacting the tissue in vivo with an emulsion of the application under conditions such that the fluorocarbon imaging reagent becomes associated with the tissue.

In certain aspects, the application discloses a method for detecting elevated vascular permeability in a tissue, the method comprising contacting the tissue in vivo with an emulsion of the application under conditions such that the fluorocarbon imaging reagent becomes associated with the tissue.

In certain aspects, the application discloses a labeled cellular formulation for administration to a subject, the formulation comprising: a) a cell; and b) an emulsion of the application that is associated with the cell.

The invention contemplates combinations of any of the foregoing aspects and embodiments of the invention.

BRIEF DESCRIPTION OF THE DRAWINGS

FIG. 10 shows quantification of the inflammation profile down the spinal cord of a rat with experimental allergic encephalomyelitis (EAE). Animals showing clinical signs of EAE (stage 2) were given an intravenous injection of nanoemulsion 3, and 48 hours later the rat was sacrificed and inflammation was assayed using high resolution $^{19}$F NMR spectra of intact, fixed segments of the spinal cord.

DETAILED DESCRIPTION

1. Overview

Figure 1:
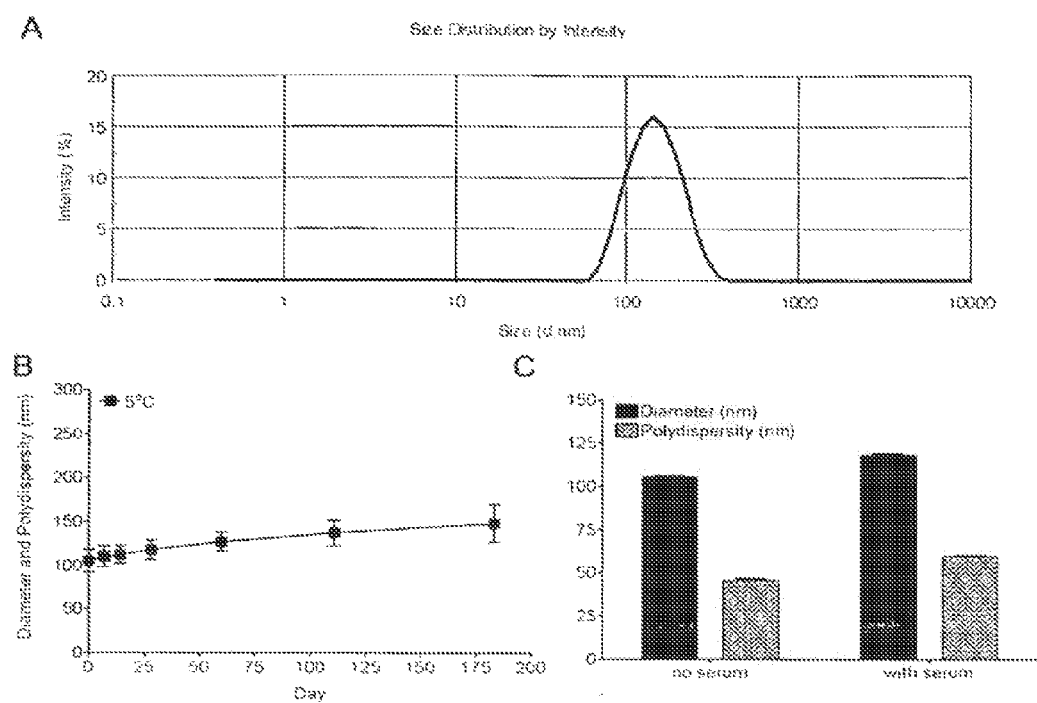
FIG. 1 shows data collected for Emulsion 3, containing perfluoro-15-crown 5 ether and emulsified with Cremophor EL, A) Dynamic light scattering (DLS) was measured to show emulsion droplet size distribution. B) Long term stability (6 months) at standard storage temperature 5° C. was assessed. These data show the measured average diameter and polydispersity (both in units of nm) over time. C) Serum stability of emulsion was assessed by measuring diameter and polydispersity in presence of serum by DLS. Data are the average of n=3 independent measurements and displayed as the mean ± standard deviation (SD).

In certain aspects, the disclosure provides novel methods and reagents for labeling cells ex vivo with a nuclear magnetic resonance imaging reagent, such as a fluorocarbon imaging reagent, and quantifying the labeled cells in vivo or ex vivo. Labeled cells may be detected by a $^{19}$F nuclear magnetic resonance technique (e.g., MRI/MRS) and quantified according to methods described herein. $^{19}$F nuclear magnetic resonance techniques are excellent imaging tools for biological systems because of the absence of endogenous background signals. Fluorine is present, if at all, at exceedingly low levels in living organisms, and generally not in a chemical form that is detectable by liquid-state nuclear magnetic resonance techniques. This is quite distinct from conventional $^1$H MRI which, while providing visualization of fine anatomical detail, does not permit selective detection of particular cell populations. Certain methods disclosed herein permit whole or partial body screening to visualize the distribution of labeled cells in a living subject. The precise anatomical location of labeled cells detected by $^{19}$F nuclear magnetic resonance maybe determined by, for example, superimposition of a $^1$H MRI image that provides anatomical detail. In preferred embodiments, the $^1$H image is acquired during the same imaging session as the $^{19}$F image (without moving the subject) to ensure registration. Additionally, the nuclear magnetic resonance techniques disclosed herein may be applied effectively in ex vivo contexts, as in the case of tissue samples, excised organs and cell cultures. The imaging technology disclosed herein may be applied to a large number of biological and medical problems.

It certain aspects, a method of the invention may comprise labeling cells ex vivo with a $^{19}$F imaging reagent, administering the labeled cells to a subject, and detecting labeled cells in the subject. The cells to be labeled may be a crude cellular fraction or tissue sample, or the cells may be cultured and/or subjected to enrichment prior to labeling. For example, particular cell types may be selected by fluorescence activated cell sorting (FACS) prior to labeling. Other sorting or selective enrichment methods are known in the art for the various different cell types that may be of interest. The types of cells that are labeled may also be controlled by the nature of the imaging reagent. For example, simple colloidal suspensions of imaging reagent will tend to be taken up more quickly by cells with phagocytic activity. As another example, an imaging reagent may be formulated with or covalently bound to a targeting moiety that facilitates selective targeting of the imaging reagent to a particular population of cells. Imaging reagents are described further below. After labeling, cells may be immediately administered or the cells may be stored, further cultured, purified, enriched, segregated or processed in any way that is not incompatible with the intended use of such cells.

In certain aspects, labeled cells will be administered for a therapeutic purpose. Technology described herein may be used for monitoring the trafficking of cellular therapeutics in vivo or so any other desired milieu, such as a tissue explant. Bone marrow cell transplants have been widely used for many years in recipients of ablative therapies for cancers. Various purified cell populations have also been used in place of bone marrow, such as cell populations enriched for hematopoietic stem cells; for example cells may be harvested from umbilical cord blood or peripheral blood. After entering the bloodstream, the stem cells generally travel to the bone marrow, where they begin to produce new white blood cells, red blood cells, and platelets. This engraftment usually occurs within about 2 to 4 weeks after transplantation. Traditionally, engraftment is monitored by testing blood counts on a frequent basis, and complete recovery of immune function generally requires several months (for autologous transplant recipients) to years (for patients receiving allogeneic or syngeneic transplants). Cell sampling by horse marrow aspiration can provide further information on the function of the transplanted cells. These monitoring techniques may be enhanced by ex vivo labeling of the cells to be transplanted (or some small fraction of such cells), thus permitting non-invasive monitoring of the location and movement of transplanted cells by nuclear magnetic resonance techniques. Non-myeloablative allogeneic transplantation (i.e. reduced-intensity transplant) is a similar cell therapy that can be effective for treating several types of cancer. Generally, this technique relies on a lower dose of radiation and/or chemotherapeutic and a limited graft-versus-host disease (the action of immune cells from the transplant against any residual host cancer cells) to provide sufficient anti-cancer activity, as well as the hematopoietic potential of the graft cells to restore the patient's hematopoietic system. As with a traditional ablative graft, the techniques of the present invention may be used to monitor the locations and movements of graft cells in a non-myeloablative allogeneic transplantation.

Cellular therapeutics are also in development for use in the delivery of therapeutic proteins. In one embodiment, cells can be isolated, grown in quantity ex vivo and then implanted to produce and secrete soluble factors, which may be active either locally (e.g. enzymes, cytokines, and neurotransmitters) or at a distance (e.g. hormones and growth regulators). Cells may also be administered to a patient in order to accomplish complex therapeutic purposes, such as reconstruction of tissues, organs, or immune responses based on their ability to home to specific sites within the body, exit from the circulation, and integrate into surrounding tissue or differentiate to replace damaged tissue. Stem cell therapies have also been proposed for myriad diseases including neurological disorders, particularly those characterized by cell death (e.g., Parkinson's disease, stroke and brain injury caused by trauma), cardiovascular disorders (e.g., myocardial infarction), muscle regeneration (e.g., in patients suffering from cachexia or other wasting disorders), pancreatic regeneration in diabetes, liver regeneration, etc. In each instance, cells, or a sub-population thereof, may be labeled with an imaging reagent ex vivo prior to administration, thus allowing the monitoring of these cells in vivo. In vivo monitoring by a nuclear magnetic resonance technique may be useful, for example, to evaluate the viability of the administered cells. A doctor may tailor a dosing schedule depending on the degree to which labeled cells are detected in a patient after administration. In vivo monitoring may also be useful in determining whether therapeutic cells have localized to a desired location. In general, it will be possible to investigate correlations between the migration behavior of therapeutic cells in vivo, as well as the number and/or survivorship of therapeutic cells in vivo, and therapeutic outcomes. When such correlations have been established, the in vivo imaging of therapeutic cells may be used as a prognostic indicator that may be helpful in selecting the appropriate dosage, administration modes and additional therapeutic interventions that will benefit the patient. Certain imaging advances of the invention will benefit a broad range of cellular therapeutic strategies because these imaging methodologies will be able to detect when, where and if the therapeutic cells have been delivered to the desired targets in vivo. Additionally, the detection of labeled cells may be enhanced by quantification of labeled cells in a ROI, such as a particular organ or tissue.

One example of an application of technology disclosed herein is in tracking dendritic cells (DCs). DCs are known to be the most efficient antigen presenting cells and have the capacity to stimulate naive T cells to initiate an immune response. Because DCs are the most potent stimulators of immune response in the body, DCs represent a possible therapeutic approach to increasing the "visibility" of tumors to a patient's immune system. DCs are the focus of tumor vaccines in development. Varying methods are used to expose the dendritic cells to tumor antigens ex vivo, after which educated dendritic cells are reinfused to stimulate development of T-cell mediated tumor killing. Data applying art embodiment of the present disclosure to the labeling and tracking of DCs and other cell types, presented in WO2005072780, is incorporated by reference herein.

In addition to DCs, other cell types have demonstrated promise for immunotherapy in cancer and other diseases such as diabetes, although their progress has been hampered by many factors, including the inability to observe their movement following transplantation into animals and humans. Natural killer (NK) cells, when harvested, treated ex vivo, and transplanted, have demonstrated the ability to kill metastatic tumor cells. Additional cell types treated ex vivo and transplanted to promote cancer immunity include lymphokine-activated killer (LAK) cells, tumor-infiltrating lymphocytes, and activated killer monocytes. Transplantation of T cells, which are white blood cells that attack pathogenic cells, has demonstrated promise against a variety of cancers, including pancreatic cancer, in which clinical trials are beginning, and against multiple sclerosis and HIV infection.

In certain aspects, labeled cells are administered to a subject for non-therapeutic purposes. For example, cells may be labeled ex vivo, administered to a subject and then detected, with the expectation that the labeled cells will behave similarly to like, unlabeled cells in vivo and may therefore be used to monitor the behavior of endogenous cell populations. Monitoring may be used for the purpose of tracking movements of cells, particularly in the case of cells that are known to be highly mobile, such as cells of the immune system, many types of stem cells and blood born cells. Monitoring may also be used for the purpose of tracking viability or adherence of non-mobile cells at the site of implant. Cells of many tissues, such as muscle, liver, pancreas, kidney, brain or skin will tend to be relatively stationary, but disappearance of label may indicate a high death rate, low adherence, or other information. Modern cell culture and sorting techniques allow the selective pooling and labeling of virtually any desired cell population, including various stem cell types, immune cell types, and other blood cell types. For example, cell surface markers can be used to sort mixed populations of cells to purify a population of interest. As described in WO2005072780 and US provisional application No. 60/792,003 (both of which are herein incorporated by reference in their entirety), both T cells and dendritic cells may be labeled ex vivo and detected in vivo.

As an example, labeled immune cells may be used as detectable proxies for the movements of immune cells in a patient. Immune cells participate in and are markers for a host of inflammatory and autoimmune disorders, as well as cancer and atherosclerotic plaque formation. As a general methodology, any process involving the recruitment of immune cells may be detected in a patient by administering to the patient labeled immune cells. The accumulation of label in a particular area provides art indication of the degree of immune response occurring in that portion of the body. Traditionally, these types of studies involve histological techniques than are incompatible with living subjects. Certain methods of the disclosure may facilitate the development of therapeutic strategies tor the treatment of human diseases. The ability to track selected populations of immune cells non-invasively, and without the use of radioisotopes, can impact many areas of basic and clinical immunology, such as multiple sclerosis, diabetes, monitoring organ transplant rejection, and cancer. For instance, tumors are often highly infiltrated by immune cells. Labeled cells may be imaged in a subject to reveal the location of a tumor, and in some instances may be useful as a non-invasive detection screen. Early detection of cancels has been a critical problem, as most early stage cancers are readily treated by surgery without resort to debilitating chemotherapeutic agents. Likewise, the progress of other inflammatory diseases may be monitored by tracking the dynamics of immune cells in the patient. The effectiveness of immunosuppressant therapy may be assessed as well. In the instance of an organ transplant recipient, the recipient could receive a dose of labeled immune cells prior to receiving the transplantation. In vivo monitoring of the accumulation of immune cells in the transplant could then be used as an early warning sign of rejection. In the case of transplants, the methods disclosed herein are particularly desirable because the alternative, biopsies, are well-known to increase the risk of organ rejection.

As an additional example, cells for use in a bone marrow cell transplant or a peripheral blood stem cell transplant, may be labeled ex vivo as described herein, administered, and monitored in vivo by a nuclear magnetic resonance technique. Such monitoring may be used to evaluate the engraftment of donor cells in the recipient bone cavities, as well as survivorship and movement of labeled cells in the recipient. A physician can use information relating to the trafficking of donor cells in a recipient as an early indication of the likely success or failure of the procedure. This type of early detection will allow physicians to tailor the post-transplant therapeutic regimen accordingly. Another cellular cancer therapeutic, where the detection technology can be applied is the allogeneic non-myeloablative, or reduced intensity transplant. This procedure may be used with a donor lymphocyte infusion to boost graft-verses-tumor effect which destroys cancer cells. Here the entire population, or a fraction, of transplanted cells could be labeled before infusion. A nuclear magnetic resonance technique could then be used determine where the cells traffic to in the body, which can be indicative of the efficacy of the procedure. As it is often desirable to limit the dose of allogeneic cells to minimize rejection, the cell's trafficking pattern may be used to calibrate dose. In the above cancer cell therapies it may be desirable to selectively label one or more sub-population of the transplanted cells (e.g., CD34+ stem cells or T cells) that are believed to have therapeutic efficacy.

As a further example, cells involved in formation of new tissue, such as in angiogenesis, can be labeled, administered to a subject, and detected to identify hotspots of tissue formation. For example, smooth muscle cells and/or endothelial precursor cells may be labeled and introduced into the bloodstream. Such cells are expected to accumulate at sites of angiogenic activity. Angiogenic activity may be associated with physiological and pathological events such as menstrual cycling, early pregnancy, collateral vessel formation in response to arterial blockages, tumor development and wound healing. Similarly, cells involved in wound healing, such as fibroblasts, may be labeled and administered systemically or to a site of suspected injury in order to monitor cellular behavior.

For example, a medicament or delivery device containing labeled cardiomyocyte lineage cell aggregates or cells derived therefrom may be provided for treatment of a human or animal body, including formulations for cardiac therapy. Cardiomyocyte lineage cells may be administered to a patient in a method for reconstituting or supplementing contractile and/or pacemaking activity in cardiac tissue (see US Patent Application No. 20060040389, 20050112104, 20050244384, which are incorporated in their entirety herein).

In accordance with the present invention labeled cardiomyocyte lineage cells are used to regenerate or repair striated cardiac muscle that has been damaged through disease or degeneration. The labeled cardiomyocyte lineage cells integrate with the healthy tissue of the recipient to replace the function of the dead or damaged cells, thereby regenerating the cardiac muscle as a whole. Cardiac muscle does not normally have reparative potential. The labeled cardiomyocyte lineage cells are used, for example, in cardiac muscle regeneration, for a number of principal indications: (i) ischemic heart implantations, (ii) therapy for congestive heart failure patients, (iii) prevention of further disease for patients undergoing coronary artery bypass graft, (iv) conductive tissue regeneration, (v) vessel smooth muscle regeneration and (vi) valve regeneration.

The administration of the cells can be directed to the heart, by a variety of procedures. Localized administration is preferred. The mesenchymal stem cells can be from a spectrum of sources including, in order of preference: autologous, allogeneic, or xenogeneic. There are several embodiments to this aspect, including the following. The present invention allows monitoring of the progress of these cell in vivo.

The cardiomyocyte lineage cells may be cardiomyocyte precursor cells, or differentiated cardiomyocytes. Differentiated cardiomyocytes include one or more of primary cardiomyocytes, nodal (pacemaker) cardiomyocytes; conduction cardiomyocytes; and working (contractile) cardiomyocytes, which may be of atrial or ventricular type. In certain embodiments, cells come from a muscle sample (or other sample) that contains muscle progenitor cells such as satellite cells (see US Patent Application No. 20050244384). In certain embodiments, cells are mesenchymal stem cells (MSCs) (see US Patent Application No. 20050112104).

A "cardiomyocyte precursor" is defined as a cell that is capable (without dedifferentiation or deprogramming) of giving rise to progeny that include cardiomyocytes. Such precursors may express markers typical of the lineage, including, without limitation, cardiac troponin 1 (cTn1), cardiac troponin T (cTnT), sarcomeric myosin heavy chain (MHC), GATA4, Nkx2.5, N-cadherin, .beta.1-adrenoceptor (.beta.1-AR), ANF, the MEF-2 family of transcription factors, creatine kinase MB (CK-MB), myoglobin, or atrial natriuretic factor (ANF).

In certain instances, cells may prove to be so thoroughly associated with a biological site or structure of interest that the labeled cells may be administered for the sole purpose of aiding in the visualisation of such a structure. As mentioned above, immune cells characteristically infiltrate tumors. Accordingly, labeled immune cells may be administered for the purpose of visualizing tumors.

Technology disclosed herein may be applied to studies of animal models of human diseases. Various animal models of diseases may evince altered dynamics or survival of one or more cell populations. Such cell populations may be labeled, administered to the animal and monitored. For example, the infiltration of immune cells into the pancreas of the NOD mouse model for diabetes may be monitored. Other examples of animal models include: experimental allergic encephalomyelitis (multiple sclerosis model), gliosarcoma tumor models, and organ-transplant rejection. By tracking phenotypically-defined populations of immune cells in these models, one can elucidate aspects of the disease etiology and monitor how cell trafficking is affected by therapeutics. This method may be used, for example, to screen for drugs that have a desired effect in an animal model. A drug screening assay may comprise administering labeled cells to an animal and detecting the cells in vivo in the presence of a test agent. Changes in cell behavior that are correlated with the presence of the test agent may be indicative of a therapeutic effect. Such changes may be detected by comparison to a suitable reference, including, for example, the same animal before and after treatment with the test agent or a separate, untreated animal. In addition to a test agent, the methods may be used to evaluate the effects of test conditions, such as an exercise regimen, injury, genetic alteration, etc. As an example, it is expected that a drug for treatment of an autoimmune disease would decrease the tendency of immune cells to accumulate in an affected tissue. In addition to steady state evaluations, methods disclosed herein may be used to evaluate kinetic properties of cells, such as the rate at which cells arrive at a particular site and the time of signal persistence at a site. Drug screening assays may be particularly powerful when combined with in vivo monitoring of tightly defined cell populations, such as certain groups of immune cells that are implicated in various disorders. For example, monitoring of labeled cytotoxic T cells may be particularly useful in identifying drugs that may be useful in preventing transplant rejection. The ability to monitor cells in vivo provides a powerful assay that may be applied to the analysis of essentially any experimental animal, including, for example, any of the various transgenic or otherwise mutant mice that have been generated.

Several groups have studied labeling and visualising immune cells using MRI contrast agents. Other researchers have used MRI contrast agents to label cell types such as stem cells and neuronal precursors. The majority of these studies render the cells magnetically-distinct via the incorporation of superparamagnetic iron-oxide (SPIO) agents. Cells labeled with contrast agents incorporating other types of metal ions, particularly gadolinium and manganese have also been used. In studies utilizing these metal-ion based agents, the compounds are not directly imaged; instead, one observes their indirect effect on surrounding waters. The presence of the agent tends to shorten the relaxation times ($T_1$, $T_2$, or $T_2^*$) of water in proximity to the compound; these effects can be detected in relaxation time-weighted images. SPIO agents, for example, impart contrast to conventional $^1H$ images by locally perturbing the magnetic field experienced by the nearby mobile water molecules, which in turn modulates $T_1$, $T_2$, or $T_2^*$. Methods described herein are distinctly different from all methods using metal-ion based contrast agents because signals from $^{19}F$ nuclei in the imaging reagents may be directly detected and, optionally, imaged.

An inherent drawback to defecting labeled cells using metal-ion based contrast agents is that one is often in a situation where it is necessary to interpret subtle changes in grayscale contrast in regions that are believed to contain labeled cells. The large $^1H$ background signal from the high concentration of mobile water present in tissues can make it difficult to unambiguously identify regions containing labeled cells; this is especially problematic if the labeled cell biodistribution is not known a priori. The results of a 'snapshot' image are often ambiguous as to whether labeled cells are present in a specific tissue. This is a particularly vexing problem when trying to detect SPIO labeled cells in iron-laden organs that intrinsically appear dark in anatomical ($T_2$- or $T_2^*$-weighted) images, such as in the liver or the spleen. Often one must resort to detecting the time-lapse image intensity changes in a particular organ over a period of several hours to verify that labeled cells have accumulated. Furthermore, quantification of labeled cells in viva in regions of interest using metal-ion based contrast agents is problematic, and there is generally no simple and reliable way to do this using relaxation-time weighted MRI or by using quantitative relaxation-time MRI maps.

In certain embodiments, the compositions of the application may find application in $^{19}F$-NMR spectroscopy (MRS), imaging (MRI), and spectroscopic imaging (MRSI).

In another aspect of the application, the emulsions of the application may be used for in situ labeling of resident macrophages and monocytes. In this application, a bolus of emulsion is directly injected intravenously (iv). Here, the emulsion is buffered appropriately (e.g., a physiologically safe pH, osmality, etc.) for safe iv injection. Following injection, the emulsion droplets are scavenged from the blood by resident phagocytic cells, such as neutrophils, macrophages and monocytes. These labeled cells participate in inflammatory events within the body. When sufficient numbers of these in situ labeled cells accumulate at a site, they become detectable using $^{19}F$ MRI/MRS in vivo or in excised (biopsied, necropsied tissue). The absolute number of $^{19}F$ nuclei or the amount of $^{19}F$ signal present in a tissue (measured in vivo or ex vivo) directly correlates to the degree or extent of inflammation present. In certain embodiments, the $^{19}F$ signal is an inflammation diagnostic, quantitative biomarker or index of inflammation.

In certain embodiments, an emulsion bolus is injected iv, and the emulsion droplets are taken up by resident phagocytes that migrate to a tumor. The detection of $^{19}F$ at the tumor is a diagnostic tool which identifies the location of the tumor as well as the distribution and extent of its macrophage or inflammation activity. Furthermore, perfluoro-15-crown-5 ether, a principal component of the emulsions, is known to coordinate or bind oxygen. It is known in the art that this molecule, in the presence of oxygen, has its $^{19}F$ NMR relaxation times (T1, T2 and T2*) shortened by an amount that is linearly proportional to the local partial pressure of oxygen (pO2). In particular, the $^{19}F$ spin-lattice relaxation time (T1) of perfluoro-15-crown-5 ether is very sensitive to pO2 (C. H. Sotak, et al., *Magn. Reson. Med.* 29, 188 (1993)). Thus, T1 measurements of the interstitial and macrophage-incorporated perfluoro-15-crown-5 ether in the tumor may be used to measure pO2, which can be a sensitive marker of the efficacy of a variety of cancer therapeutics. In certain embodiments, emulsions of the application may be used to assay hypoxia or hyperoxia. In certain embodiments, pO2 sensing of tissues is achieved by direct injection of emulsions into tissue.

The emulsions of the application may be used to detect a wide range of lesions and diseases where inflammation is present. In certain such embodiments, the disease is selected from the group consisting of cancer, cardiovascular disease, inflammatory bowel disease, autoimmune disease (e.g., multiple sclerosis, rheumatoid arthritis, type-1 diabetes, lupus, Crohn's disease, optic neuritis, etc.), organ transplant rejection, infectious diseases, and traumatic brain and spinal cord injury.

In certain embodiments, emulsions of the application may be used to image lesions of the liver via a $^{19}F$ image of the emulsion distribution in that organ. Emulsions of the application which are injected iv may be cleared by the liver and taken up by liver cells. Lesions of the liver may result in anomalous and heterogeneous distributions of emulsion uptake and $^{19}F$ image intensity.

In a further aspect of the application, the emulsions of the application may be used as a probe of tissue oxygenation. In certain embodiments, the emulsions of the application can serve as a sensor for pO2 in tissue using $^{19}F$ MRS/MRI. Perfluoro-15-crown-5 ether coordinates oxygen, thereby changing its $^{19}F$ T1-value several fold. Thus, a measurement of the $^{19}F$ T1 either by MRS or MRI (e.g., using an image map of T11) provides a quantitative measurement of pO2. (see Taylor J, and Deutsch C. Biophys J 53; 227-233, 1988; Mason, R. P.; Rodbumrung, W.; Antich, P. P. NMR. Biomed 9:125-134; 1996; Lankemper-Ostendorf S.; Scholz, A.; Burger, K.; Heussel, C. P.; Schmittner, M.; Weiler, N.; Markstaller, K.; Eberle, B.; Kauczor, H. U.; Quintel, M.; Thelen, M.; Sehreiber, W. G. Magn Reson Med 47:82-89; 2002; and Kim, J. G.; Zhao, D.; Song, Y.; Constantinesco, A.; Mason, R. P.; Liu, H. J Biomed Opt 8:53-62; 2003; all of which are incorporated herein by reference).

In another aspect of the application, emulsions of the application accumulate in areas with elevated vascular permeability, such as, e.g., in tumors. In certain embodiments, emulsions of the application may be used to assay the perfusion of tissues, provide the possibility of determining the blood volumes in tissues, to selectively shorten the relaxation times or densities of the blood and to graphically visualize the permeability of blood vessels. In certain embodiments, emulsions of the application may be used for specific diagnosis of malignant tumors, early therapy control in cytostatic, antiphlogistic or vasodilatative therapy, early detection of underperfused areas (e.g., in the myocardium), angiography in vascular diseases, and detection and diagnosis of sterile or infectious inflammations.

In yet another aspect of the application, the emulsions of the application may be used as an artificial oxygen carrier or artificial blood substitute (See US Patent Publication No. 20040057906, U.S. Pat. Nos. 4,838,274 and 5,785,950 and WO 96/40057 all of which are incorporated herein by reference). In certain embodiments, the emulsions may be used in vivo or ex vivo. The emulsions of the disclosure are capable of having dissolved in them large amounts of gases, including oxygen, carbon dioxide, and air, per unit volume. Accordingly, fluorocarbons (FCs) and perfluorocarbons (PFCs) may be used as carriers in applications wherein oxygen must be supplied to organs and tissues.

Thus the methods and compositions disclosed herein provide much needed tools in the fields of medicine and biology.

2. Emulsions

The imaging reagent used in the subject methods is a fluorocarbon, i.e., a molecule including at least one carbon-fluorine bond. By virtue of the $^{19}$F atoms, the imaging reagents disclosed herein may be detected by $^{19}$F MRI and other nuclear magnetic resonance techniques, such as MRS techniques. In certain preferred embodiments, a fluorocarbon imaging reagent will have one or more of the following properties: 1) reduced cytotoxicity; 2) a $^{19}$F NMR spectrum that is simple, ideally having a single, narrow resonance to minimize chemical shift artifacts; 3) high sensitivity with a large number of NMR-equivalent fluorine atoms in each molecule; 4) formulated to permit efficient labeling of many cell types and not restricted to phagocytic cells. Preferably, the imaging reagent comprises a plurality of fluorines bound to carbon, e.g., greater than 5, greater than 10, greater than 15 or greater than 20 fluorines bound to carbon. Preferably, at least 4, at least 8, at least 12 or at least 16 of the fluorines have a roughly equivalent NMR chemical shift.

For labeling cells in culture, the imaging reagents can be employed in one or more of at least three modalities: 1) imaging reagents that are internalized or otherwise absorbed by target cells without the formation of any covalent or other binding association; 2) imaging reagents that covalently attach to target cells; and 3) imaging reagents coupled to molecules, such as antibodies or ligands, that bind to molecules present on the target cells.

Imaging reagents of the first type include the perfluoro crown ethers and other perfluoropolyethers (PFPEs) that are taken up by cells and, preferably, are retained in the cell without degradation for a substantial period of time, e.g., having a half-life in the cell of at least 1 hour, at least 4 hours, at least about a day, at least about three days, or even at least about a week. For obvious reasons, it is preferred that the imaging reagent not interfere with ordinary cellular functions or exhibit cytotoxicity at the concentrations employed for labeling. As demonstrated herein, perfluoropolyethers show reduced toxic effect on the labeled cells.

Imaging reagents of the second type include electrophilic compounds that react with nucleophilic sites on the cell surface, such as exposed thiol, amino, and/or hydroxyl groups. Accordingly, imaging reagents such as maleimides, alkyl iodides, N-hydroxysuccinimide or N-hydroxysulfosuccinimide esters (NHS or sulfo-NHS esters), acyl succinimides, and the like can form covalent bonds with cell surfaces. Other techniques used in protein coupling can be adapted for coupling imaging reagents to cell surface proteins. See Means et al. (1900) *Bioconjugate Chemistry* 1:2-12, for additional approaches to such coupling.

Imaging reagents of the third type can be prepared by reacting imaging reagents of the second type not with the cells themselves, but with a functional moiety that is cell-targeting ligand or antibody. Suitable ligands and antibodies can be selected for the application of interest. For example, a ligand that selectively targets hematopoietic cells could be labeled with an imaging reagent as described herein and administered to a patient such as by infection.

Alternatively, an imaging reagent can be coupled to an indiscriminate internalizing peptide, such as antepennepedia protein, HIV transactivating (TAT) protein, mastoparan, melittin, bombolittin, delta hemolysin, pardaxin, *Pseudomonas* exotoxin A, clathrin, Diphtheria toxin, C9 complement protein, or a fragment of any of these. Cells treated with this indiscriminate molecule ex vivo will absorb the imaging reagent. When such labeled cells are implanted into an animal, such as a mammal, the imaging reagent can be used to visualize and/or track the implanted cells by nuclear magnetic resonance techniques.

In one embodiment, the internalizing peptide is derived from the drosophila antepennepedia protein, or homologs thereof. The 60-amino acid-long homeodomain of the homeo-protein antepennepedia has been demonstrated to translocate through biological membranes and can facilitate the translocation of heterologous polypeptides to which it is coupled. See for example Derossi et al, (1994) *J Biol Chem* 269:10444-10450; and Perez et al. (1992) *J Cell Sci* 102:717-722. It has been demonstrated that fragments as small as 16 amino acids long of this protein are sufficient to drive internalization. See Derossi et al, (1990) *J Biol Chem* 271:18188-18193.

Another example of an internalizing peptide is the HIV transactivator (TAT) protein. This protein appears to be divided into four domains (Kuppuswamy et al. (1989) *Nucl. Acids Res.* 17:3551-3561). Purified TAT protein is taken up by cells in tissue culture (Frankel and Pabo, (1989) *Cell* 55:1189-1193), and peptides, such as the fragment corresponding to residues 37-62 of TAT, are rapidly taken up by cell in vitro (Green and Loewenstein, (1989) *Cell* 55:1179-1188). The highly basic region mediates internalization and targeting of the internalizing moiety to the nucleus (Ruben et al., (1989) *J. Virol* 63:1-8). Peptides or analogs that include a sequence present in the highly basic region can be conjugated to fluorinated imaging reagents to aid in internalization and targeting those reagents to the intracellular milieu.

The present invention provides novel compositions comprising imaging reagents. For example, the present invention provides an aqueous composition comprising perfluoro-15-crown-5 ether or PFPE oxide, an emulsifier, a surfactant co-mixture, and an additive, in certain embodiments, the surfactant co-mixture comprises lecithin (i.e., lipoid egg phosphatidyl choline), cholesterol, and dipalmltoyl phosphatidylethanolamine (DPPE). In certain such embodiments, the surfactant co-mixture comprises 70 mol % of lecithin; 28 mol % of cholesterol; and 2 mol % of DPPI. In certain embodiments, the additive is propylene glycol.

As used herein, the term "PFPE oxide" refers to perfluoropoly(ethylene glycol) Dialkyl Ether (e.g., as can be purchased from Extfuor Inc., TX),

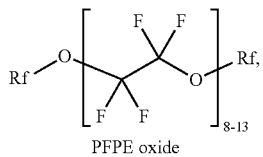

PFPE oxide (Rf = CF₃, CF₂CF₃)

wherein Rf is $CF_3$ and $CF_2CF_3$ in a ratio of 2:1, based on $^{19}F$ NMR analysis.

In certain embodiments, the emulsifier is also a non-ionic solubiliser. In certain embodiments, the emulsifier comprises glycerol polyethylene glycol ricinoleate. In certain such embodiments, the emulsifier further comprises fatty acid esters of polyethylene glycol, free polyethylene glycols, and ethoxylated glycerol. In certain embodiments, the emulsifier is prepared by reacting castor oil and ethylene oxide in a molar ratio of 1:35. Exemplary emulsifiers can be obtained from BASF Corporation and are sold under the trade name of Cremophor® EL.

In certain embodiments, the aqueous composition comprising perfluoro-15-crown-5 ether or PFPE oxide, Cremophor® EL, a surfactant co-mixture (e.g., comprising lecithin, cholesterol, and DPPE), and an additive (e.g., propylene glycol) comprises perfluor-15-crown-5 ether or PFPE oxide in the range of 20% to 50% w/v, such as 25% to 45% w/v, such as 30% to 40% w/v, such as 30%, 31%, 32%, 33%, 34%, 35%, 36%, 37%, 38%, 39% or 40% w/v. In certain such embodiments, the aqueous composition comprising perfluoro-15-crown-5 ether or PFPE oxide, Cremophor® EL, a surfactant co-mixture (e.g., comprising lecithin, cholesterol, and DPPE), and an additive (e.g., propylene glycol) comprises perfluor-15-crown-5 ether or PFPE oxide in the range of 35% to 36% w/v, such as 35.1%, 35.2%, 35.3%, 35.4%, 35.5%, 35.6%, 35.7%, 35.8%, or 35.9% w/v. In certain embodiments, the aqueous composition comprising perfluoro-15-crown-5 ether or PFPE oxide, Cremophor® EL, a surfactant co-mixture (e.g., comprising lecithin, cholesterol, and DPPE), and an additive (e.g., propylene glycol) comprises perfluor-15-crown-5 ether pr PFPE oxide in 35.6% w/v.

In certain embodiments, the aqueous composition comprising perfluoro-15-crown-5 ether or PFPE oxide, Cremophor® EL, a surfactant co-mixture (e.g., comprising lecithin, cholesterol, and DPPE), and an additive (e.g., propylene glycol) comprises Cremophor® EL in the range of 1% to 10% w/v, such as 1% to 5% w/v, such as 1%, 2%, 3%, 4%, or 5% w/v. In certain embodiments, the aqueous composition comprising perfluoro-15-crown-5 ether or PFPE oxide, Cremophor® EL, a surfactant co-mixture (e.g., comprising lecithin, cholesterol, and DPPE), and an additive (e.g., propylene glycol) comprises Cremophor® EL in 3% w/v.

In certain embodiments, the aqueous composition comprising perfluoro-15-crown-5 ether or PFPE oxide, Cremophor® EL, a surfactant co-mixture (e.g., comprising lecithin, cholesterol, and DPPE), and propylene glycol comprises propylene glycol in the range of 1% to 10% w/v, such as 1% to 5% w/v, such as 1%, 2%, 3%, 4%, or 5% w/v. In certain embodiments, the aqueous composition comprising perfluoro-15-crown-5 ether or PFPE oxide), Cremophor® EL, a surfactant co-mixture (e.g., comprising lecithin, cholesterol, and DPPE), and propylene glycol comprises propylene glycol in 2% w/v.

In certain embodiments, the aqueous composition comprising perfluoro-15-crown-5 ether or PFPE oxide, Cremophor® EL, an additive (e.g., propylene glycol), and a surfactant co-mixture, wherein the surfactant co-mixture comprises lecithin, cholesterol, and DPPE, comprises the surfactant co-mixture, wherein the surfactant co-mixture comprises lecithin, cholesterol, and DPPE, in the range of 1% to 10% w/v, such as 1% to 5% w/v, such as 1%, 2%, 3%, 4%, or 5% w/v. In certain embodiments, the aqueous composition comprising perfluoro-15-crown-5 ether or PFPE oxide, Cremophor® EL, an additive (e.g., propylene glycol), and a surfactant co-mixture, wherein the surfactant co-mixture comprises lecithin, cholesterol, and DPPE, comprises the surfactant co-mixture, wherein the surfactant co-mixture comprises lecithin, cholesterol, and DPPE, in 2% w/v.

In certain embodiments, the aqueous composition comprising perfluoro-15-crown-5 ether or PFPE oxide, Cremophor® EL, a surfactant co-mixture (e.g., comprising lecithin, cholesterol, and DPPE), and an additive (e.g., propylene glycol) further comprises polyethylamine. In certain such embodiments, the aqueous composition comprises polyethylamine in the range of 0.01% to 5.0% w/w. In certain embodiments, the aqueous composition comprising perfluoro-15-crown-5 ether or PFPE oxide, Cremophor® EL, a surfactant co-mixture (e.g., comprising lecithin, cholesterol, and DPPE), an additive (e.g., propylene glycol), and polyethylamine further comprises protamine sulfate. In certain such embodiments, the aqueous composition protamine-sulfate in the range of 0.01% to 5.0% w/w.

In certain embodiments, the present invention provides an aqueous composition comprising perfluoro-15-crown-5 ether or PFPE oxide in 35.6% w/v, Cremophor® EL in 3.0% w/v, a surfactant co-mixture (e.g., comprising lecithin, cholesterol, and DPPE) in 2.0% w/v, and an additive (e.g., propylene glycol) in 2.0% w/v.

The terms emulsion and nanoemulsion as used in this application are equivalent unless specifically stated otherwise. In certain embodiments, the emulsion may further comprise a block copolymer of polyethylene and polypropylene glycol. In certain embodiments, the emulsion may further comprise a Plutonic™. Nonionic Pluronic™ surfactants, polyethyleneoxide (PEO)/polypropyleneoxide (PPO)/polyethyleneoxide (PEO) block (ABA type), (PEO/PPO/PEO) block copolymers, exhibit a wide range of hydrophilicity/hydrophobicity as a function of the PEO/PPO ratio, so that one can expect to obtain different phase separated morphologies with polymers such as PLA as well as different degrees of hydration of the matrix. In particular, hydration plays an important role in determining polymer degradation via hydrolysis of the ester backbone. These polymeric surfactants exhibited minimal toxicities in vivo and some of them are in clinical use, as described by BASF Corporation in their 1989 Technical Bulletin; Attwood, et al., Int. J. Pharm. 26, 25 (1985); and U.S. Pat. No. 4,188,373 to Krezanoski. These materials can be obtained from BASF Corporation. In certain embodiments, emulsions of the present invention further comprise tri-block copolymer which comprises polyethyleneoxide and polypropyleneoxide.

In certain embodiments, emulsions of the present invention comprise a tri-block copolymer of poly(ethylene oxide)-poly(propylene oxide)-poly(ethylene oxide) (PEO-PPO-PEO)

comprising 80% PEO content. In certain such embodiments, the hydrophilic-lipophilic balance (HLB) value of the tri-block copolymer is 29, wherein the HLB value can be calculated from the following equation:

$$HLB = -36\frac{m}{2n+m} + 33$$

where n represents the number of repeat units in the PEO segment of the polymer and m represents the number of repeat units in the PPO segment of the polymer. Exemplary tri-block copolymers can be obtained, from BASF Corporation and are sold under the trade name of Pluronic™ F68.

The present invention further provides an aqueous composition comprising perfluoro-15-crown-5 ether or PFPE oxide and the Pluronic™ F68. In certain embodiments, the aqueous composition comprising perfluoro-15-crown-5 ether or PFPE-oxide and the Pluronic™ F68, comprises perfluoro-15-crown-5 or PFPE oxide ether in the range of 10% to 20% w/w, such as 12% to 1/% w/w, such as 12%, 13%, 14%, 15%, 16%, or 17% w/w. In certain embodiments, the aqueous composition comprising perfluoro-15-crown-5 ether or PFPE oxide and the Pluronic™ F68, comprises-perfluoro-15-crown-5 ether or PFPE oxide in 15% w/w. In certain embodiments, the aqueous composition comprising perfluoro-15-crown-5 ether or PFPE oxide and the Pluronic™ F68, comprises the Plutonic™ F68 in the range of 0.1% to 2.0% w/w, such as 0.1% to 1.0% w/w, such as 0.1%, 0.2%, 0.3%, 0.4%, 0.5%, 0.6%, 0.7%, 0.8%, 0.9% or 1.0% w/w. In certain embodiments, the aqueous composition comprising perfluoro-15-crown-5 ether or PFPE oxide and the Pluronic™ F68, comprises the Pluronic™ F68 in 0.6% w/w.

In certain embodiments, the present invention provides an aqueous composition comprising perfluoro-15-crown-5 ether or PFPE oxide in 15% w/w and the Pluronic™ F68 in 0.6% w/w.

In certain embodiments, the aqueous composition comprising perfluoro-15-crown-5 ether or PFPE oxide and the Pluronic™ F68 further comprises protamine sulfate. In certain such embodiments, the aqueous composition comprising perfluoro-15-crown-5 ether or PFPE oxide, the Pluronic™ F68, and protamine sulfate comprises protamine sulfate in the range of 0.01% to 1.0% w/w, such as 0.01% to 0.5% w/w, such as 0.01% to 0.10% w/w, such as 0.01%, 0.02%, 0,03%, 0.04%, 0.05%, 0.06%, 0.07%, 0.08%, 0.09%, or 0.10% w/w. In certain embodiments, the aqueous composition comprising perfluoro-15-crown-5 ether or PFPE oxide, the Pluronic™ F68, and protamine sulfate comprises protamine sulfate in 0.04% w/w.

In certain embodiments, the aqueous composition comprising perfluoro-15-crown-5 ether or PFPE oxide and the Pluronic™ F68 further comprises polyethylamine. In certain embodiments, the present invention provides an aqueous composition comprising perfluoro-15-crown-5 ether or PFPE oxide in 15% w/w, the Pluronic™ F68 in 0.6% w/w, and protamine sulfate in 0.04% w/w.

The present invention also provides formulations of the compositions of the present invention as described above that are suitable for uptake by cells. For example, the compositions of the present invention may be formulated as an emulsion. As an example, the present invention provides an emulsion comprising an aqueous composition comprising perfluoro-15-crown-5 ether or PFPE oxide. Cremophor® EL, a surfactant co-mixture, and an additive. In certain embodiments, the surfactant co-mixture comprises lecithin, cholesterol, and dipalmitoyl phosphatidyl ethanolamine (DPPE). In certain such embodiments, the surfactant co-mixture comprises 70 mol % of lecithin; 28 mol % of cholesterol; and 2 mol % of DPPI. In certain embodiments, the additive is propylene glycol.

In certain embodiments of the foregoing emulsion, the aqueous composition comprising perfluoro-15-crown-5 ether or PFPE oxide, Cremophor® EL, a surfactant co-mixture (e.g., comprising lecithin, cholesterol, and DPPE), and an additive (e.g., propylene glycol) comprises perfluor-15-crown-5 ether or PFPE oxide in the range of 20% to 50% w/v, such as 25% to 45% w/v, such as 30% to 40% w/v, such as 30%, 31%, 32%, 33%, 34%, 35%, 36%, 37%, 38%, 39% or 40% w/v. In certain such embodiments of the foregoing emulsion, the aqueous composition comprising perfluoro-15-crown-5 ether or PFPE oxide, Cremophor® EL, a surfactant co-mixture (e.g., comprising lecithin, cholesterol, and DPPE), and an additive (e.g., propylene glycol) comprises perfluor-15-crown-5 ether or PFPE oxide in the range of 35% to 36% w/v, such as 35.1%, 35.2%, 35.3%, 35.4%, 35.5%, 35.6%, 35.7%, 35.8%, or 35.9% w/v. In certain embodiments of the foregoing emulsion, the aqueous composition comprising perfluoro-15-crown-5 ether or PFPE oxide, Cremophor® EL, a surfactant co-mixture (e.g., comprising lecithin, cholesterol, and DPPE), and an additive (e.g., propylene glycol) comprises perfluor-15-crown-5 ether or PFPE oxide in 35.6% w/v.

In certain embodiments of the foregoing emulsion, the aqueous composition comprising perfluoro-15-crown-5 ether or PFPE oxide, Cremophor® EL, a surfactant co-mixture (e.g., comprising lecithin, cholesterol, and DPPE), and an additive (e.g., propylene glycol) comprises Cremophor® EL in the range of 1% to 10% w/v, such as 1% to 5% w/v, such as 1%, 2%, 3%, 4%, or 5% w/v. In certain embodiments of the foregoing emulsion, the aqueous composition comprising perfluoro-15-crown-5 ether or PFPE oxide, Cremophor® EL, a surfactant co-mixture (e.g., comprising lecithin, cholesterol, and DPPE), and an additive (e.g., propylene glycol) comprises Cremophor® EL in 3% w/v.

In certain embodiments of the foregoing emulsion, the aqueous composition comprising perfluoro-15-crown-5 ether or PFPE oxide, Cremophor® EL, a surfactant co-mixture (e.g., comprising lecithin, cholesterol, and DPPE), and propylene glycol comprises propylene glycol in the range of 1% to 10% w/v, such as 1% to 5% w/v, such as 1%, 2%, 3%, 4%, or 5% w/v. In certain embodiments of the foregoing emulsion, the aqueous composition comprising perfluoro-15-crown-5 ether or PFPE oxide, Cremophor® EL, a surfactant co-mixture (e.g., comprising lecithin, cholesterol, and DPPE), and propylene glycol comprises propylene glycol in 2% w/v.

In certain embodiments of the foregoing emulsion, the aqueous composition comprising perfluoro-15-crown-5 ether or PFPE oxide, Cremophor® EL, an additive (e.g., propylene glycol), and a surfactant co-mixture, wherein the surfactant co-mixture comprises lecithin, cholesterol, and DPPE, comprises the surfactant co-mixture, wherein the surfactant co-mixture comprises lecithin, cholesterol, and DPPE, in the range of 1% to 10% w/v, such as, 1% to 5% w/v, such as 1%, 2%, 3%, 4%, or 5% w/v. In certain embodiments of the foregoing emulsion, the aqueous composition comprising perfluoro-15-crown-5 ether or PFPE oxide, Cremophor® EL, an additive (e.g., propylene glycol), and a surfactant co-mixture, wherein the surfactant co-mixture comprises lecithin, cholesterol, and DPPE, comprises the surfactant co-mixture, wherein the surfactant co-mixture comprises lecithin, cholesterol, and DPPE, in 2% w/v.

In certain embodiments, the present invention provides an emulsion comprising an aqueous composition comprising perfluoro-crown-5 ether or PFPE oxide in 35.6% w/v, Cremophor® EL in 3.0% w/v, a surfactant co-mixture (e.g., comprising lecithin, cholesterol, and DPPE) in 2.0% w/v, and an additive (e.g., propylene glycol) in 2.0% w/v.

The present invention further provides an emulsion comprising an aqueous composition comprising perfluoro-15-crown-5 ether or PFPE oxide and the Pluronic™ F68. In certain embodiments of the foregoing emulsion, the aqueous composition comprising perfluoro-15-crown-5 ether or PFPE oxide and the Pluronic™ F68, comprises perfluoro-15-crown-5 ether or PFPE oxide in the range of 10% to 20% w/w, such as 12% to 17% w/w, such as 12%, 13%, 14%, 15%, 16%, or 17% w/w. In certain embodiments of the foregoing emulsion, the aqueous composition comprising perfluoro-15-crown-5 ether or PFPE oxide and the Pluronic™ F68, comprises perfluoro-15-crown-5 ether or PFPE oxide in 15% w/w. In certain embodiments of the foregoing emulsion, the aqueous composition comprising perfluoro-15-crown-5 ether or PFPE oxide and the Pluronic™ F68, comprises the Pluronic™ F68 in the range of 0.1% to 2.0% w/w, such as 0.1% to 1.0% w/w, such as 0.1%, 0.2%, 0.3%, 0.4%, 0.5%, 0.6%, 0.7%, 0.8%, 0.9% or 1.0% w/w. In certain embodiments of the foregoing emulsion, the aqueous composition comprising perfluoro-15-crown-5 ether or PFPE oxide and the Pluronic™ F68, comprises the Pluronic™ F68 in 0.6% w/w.

In certain embodiments, the present invention provides an emulsion comprising an aqueous composition comprising perfluoro-15-crown-5 ether or PFPE oxide in 15% w/w and the Pluronic™ F68 in 0.6% w/w.

In certain embodiments of the foregoing emulsion, the aqueous composition comprising perfluoro-15-crown-5 ether or PFPE oxide and the Pluronic™ F68 further comprises protamine sulfate. In certain such embodiments of the foregoing emulsion, the aqueous composition comprising perfluoro-15-crown-5 ether or PFPE oxide, the Pluronic™ F68, and protamine sulfate comprises protamine sulfate in the range of 0.01% to 1.0% w/w, such as 0.01% to 0.5% w/w, such as 0.01% to 0.10% w/w, such as 0.01%, 0.02%, 0.03%, 0.04%, 0.05%, 0.06%, 0.07%, 0.08%, 0.09%, or 0.10% w/w. In certain embodiments of the foregoing emulsion, the aqueous composition comprising perfluoro-15-crown-5 ether or PFPE oxide, the Pluronic™ F68, and protamine sulfate comprises protamine sulfate in 0.04% w/w.

In certain embodiments, the present invention provides an emulsion comprising an aqueous composition comprising perfluoro-15-crown-5 ether or PFPE oxide, in 15% w/w, the Pluronic™ F68 in 0.6% w/w, and protamine sulfate in 0.04% w/w.

In certain embodiments, the compositions and emulsions of the present invention comprise Cremophor® EL, a non-ionic solubiliser and emulsifier comprising polyethylene glycol ricinoleate, made by reacting castor oil with ethylene oxide in a molar ratio of 1:35. This material can be obtained from BASF Corporation.

In certain embodiments, the emulsion may further comprise a lipid. In certain embodiments of emulsions of the present invention that further comprise a lipid, the lipid is DMPC. In certain embodiments of emulsions of the present invention that further comprise a lipid, the emulsion further comprises a Pluronic™. In certain embodiments, the Pluronic™ is F68.

In certain embodiments, the emulsion may further comprise polyethylamine.

In certain embodiments, the emulsion may further comprise protamine sulfate. In certain embodiments of emulsions of the present invention that further comprise protamine sulfate, the emulsion further comprises a Pluronic™. In certain embodiments, the Pluronic™ is F68. In certain embodiments, the emulsion of the present invention further comprises protamine sulfate.

Emulsions of the present invention will preferably have a distribution of droplet sizes that allow adequate cellular uptake. In certain embodiments, a uniform droplet size may be advantageous. The desired degree of uniformity of droplet size may vary depending upon the application. In certain embodiments, the emulsion has a mean droplet size less than 500 nm, or less than 400 nm, or less than 300 nm, or less than 200 nm in diameter. Optionally, 25%, or 50%, or 75% or more of the droplets will fall within the selected range. Droplet sizes may be evaluated by, for example, light scattering techniques or by visualizing the emulsion droplets using EM micrographs. In certain cell types that have a relatively small amount of cytoplasm, such as most stem cells, the emulsions have a mean droplet size of less than 200 nm, or less than 100 nm, or less than 50 nm in diameter.

In certain embodiments, small droplet size is advantageous. In certain embodiments, small droplet size increases: circulation time in applications where the emulsion is injected iv. In certain embodiments, droplets are separable from cells by circulation. In certain embodiments, small droplet size increases ex vivo cell labeling. In certain embodiments, small droplet size increases uniform labeling.

Emulsions for use in cells should preferably be stable at a wide range of temperatures. In certain embodiments, emulsions will be stable at body temperature (37° C. for humans) and at a storage temperature, such as 4° C. or room temperature (20-25° C.). For example, it will often be desirable to store the emulsion at a cool temperature, in the range of 2-10° C., such as 4° C., and then warm the emulsion to room temperature (e.g., 18 to 28° C., and more typically 20 to 25° C.). After labeling of cells, the emulsion will experience a temperature of about 37° C. Accordingly, a preferred emulsion will retain the desired range of droplet sixes at temperatures ranging from refrigeration temperatures up to body temperature. In certain embodiments, the emulsion is stable at temperatures ranging from 4° C. to 37° C.

In certain embodiments, the emulsion has a polydispersity index ranging from 0.1 to 0.2.

The properties of an emulsion may be controlled primarily by the properties of the imaging reagent itself, the nature of surfactants and/or solvents used, and the type of processing device (e.g., sonicator, Microfluidixer, homogenixer, etc.). Methods for forming emulsions with certain PFPE molecules are extensively described in U.S. Pat. Nos. 5,330,681 and 4,990,283, herein incorporated by reference in their entirety. A continuous phase of a polyhydroxylated compound, such as polyalcohols and saccharides in concentrated aqueous solution may be effective. The following polyalcohols and saccharides have proved to be particularly effective; glycerol, xylitol, mannitol, sorbitol, glucose, fructose, saccharose, maltitol, dimer compounds of glycerol (di-glycerol or bis(2, 3-dihydroxypropyl) ether, solid water soluble polyhydroxylated compounds as sugars and glycerol condensation products as triglycerol and tetraglycerol. The dispersion in emulsion may be performed in the presence of conventional surfactants, including cationic, anionic, amphoteric and non-ionic surfactants. Examples of suitable surfactants include sodium lauryl sulphate, sulphosuccinate (sulphosuccinic hemiester), coco-amphocarboxyglycinate, potassium cetyl phosphate, sodium alkyl-polyoxyethylene-ether carboxylate, potassium benzalconium chloride, alkyl amidopropyl betaine, cetyl-stearilic ethoxylated alcohol, and sorbitanethoxylate(20)-mono-oleate Tween 20. While thermodynamic equations may be used to attempt to predict mixtures of imaging reagents that will give emulsions having the desired droplet sizes and stability, it is generally accepted that actual testing of various mixtures will be most effective. The emulsification of mixtures is simple and quick, permitting rapid testing of a wide range of combinations to identify those that give rise to emulsions that are suitable for use in the methods disclosed herein.

In the applications involving ex vivo labeling, preferred emulsions are designed to facilitate uptake of the imaging reagent by the subject cells. A surfactant may be designed to form stable emulsions that carry a large quantity of perfluoro-15-crown-5 ether or PFPE oxide into the aqueous phase. Additionally, it may have properties that increase the intracellular delivery of the emulsion droplets in the shortest possible incubation time. Increasing the perfluoro-15-crown-5 ether or PFPE oxide intracellular loading improves sensitivity to the labeled cells. Furthermore, minimizing the culture time can be important when working with the primary cells cultures. The efficiency of intracellular uptake depends on cell type. For example macrophages and some dendritic cells will endocytose almost any particulate, whereas other cell types of interest may only be weakly phagocytic. In either case the uptake efficiency can be boosted substantially by designing the surfactant so that the surface of the emulsion droplet has properties that promote cellular uptake in culture (i.e. "self-delivering" emulsion droplets) (see Janjie et al, JACS, 2008, 130 (9), 2832-2841 and U.S. Provisional Patent Application 61/062,710, both of which are incorporated by reference in their entirety). The emulsion droplet surface can be made to have lipophilic, or optionally cationic, properties via appropriate surfactant design. For example the surfactant can incorporate lipids, such as cationic or neutral lipids, oil-in-water emulsions, micelles, mixed micelles, or liposomes, that tend, to bind to or fuse with the cell's surface, thereby enhancing emulsion droplet uptake. The emulsion droplet surface may also incorporate cell delivery signals such as polyamines. Examples include emulsions that have polyamines, such as polyethylenimine or protamine sulfate, incorporated into the emulsion droplet's surfactant layer during processing.

In certain embodiments, a colloidal system for use as a delivery vehicle in vitro and in vivo is a liposome (i.e., an artificial membrane vesicle). The preparation and use of such systems is well known in the art. Suitable cationic lipids are described in the following and are herein incorporated in their entirety; Felgner et al., 1987, PNAS 84, 7413-7417; Eppstein et al., U.S. Pat. No. 4,897,355), (Rose, U.S. Pat. No. 5,279, 833; Eppand et al, U.S. Pat. No. 5,283,185; Gebeyehu et al., U.S. Pat. No. 5,334,761; Nante et al., U.S. Pat. No. 5,527,928; Bailey et al., U.S. Pat. No. 5,552,155; Jesse, U.S. Pat. No. 5,578,475). Other approaches include incorporation into the surfactant peptides (e.g. oligo-Arg9 and TAT-like peptides) that facilitate entry into cells, or antibodies that target specific cell surface molecules. Additionally, in certain embodiments, one can incorporate small cationic proteins into the surfactant, such as protamine sulfate, to enhance cellular uptake. Protamine sulfate is non-toxic to cells and has FDA approval for use in humans as a heparin antagonist. In certain embodiments, colloidal dispersion systems are used, such as macromolecule complexes, nanocapsules, microspheres, and beads. Other approaches for enhancing uptake of the emulsified fluorocarbons, such as by using additional transfection agents or by using electroporation of the cells, is described herein.

In preferred embodiments, emulsions have "self-delivering" properties without having to add uptake enhancing reagents. Said emulsions are preferably stable and have a shelf-life of a period of months or years.

It is understood that surfactants and uptake enhancing reagents are not meant to be exclusive groups and in some cases they may be overlapping.

3. Cells and Labeling

Methods described herein may be used with a wide range of cells, including both prokaryotic and eukaryotic cells, and preferably mammalian cells. Technologies for cell preparation include cell culture, cloning, nuclear transfer, genetic modification and encapsulation.

A partial list of suitable mammalian cells includes: blood cells, myoblasts, bone marrow cells, peripheral blood cells: umbilical cord blood cells, cardiomyocytes (and precursors thereof), chondrocytes (cartilage cells), dendritic cells, fetal neural tissue, fibroblasts, hepatocytes (liver cells), islet cells of pancreas, keratinocytes (skin cells) and stem cells. In certain preferred embodiments, the cells to be used are a fractionated population of immune cells. Recognized subpopulations of immune cells include the lymphocytes, such as B lymphocytes (Fc receptors, MHC class II, CD19+, CD21+), hELer T lymphocytes (CD3+, CD4+, CD8−), cytolytic T lymphocytes (CD3+, CD4−, CD8+), natural killer cells (CD16+), the mononuclear phagocytes, including monocytes, neutrophils and macrophages, and dentritic cells. Other cell types that may be of interest include eosinophils and basophils.

Cells may be autologous (i.e., derived from the same individual) or syngeneic (i.e., derived from a genetically identical individual, such as a syngeneic littermate or an identical twin), although allogeneic cells (i.e., cells derived from a genetically different individual of the same species) are also contemplated. Although less preferred, xenogeneic (i.e., derived from a different species than the recipient) cells, such as cells from transgenic pigs, may also be administered. When the donor cells are xenogeneic, it is preferred that the cells are obtained from an individual of a species within the same order, more preferably the same superfamily or family (e.g. when the recipient is a human, it is preferred that the cells are derived from a primate, more preferably a member of the superfamily Hominoidea).

Cells may, where medically and ethically appropriate, be obtained from any stage of development of the donor individual, including prenatal (e.g., embryonic or fetal), infant (e.g., from birth to approximately three years of age in humans), child (e.g., from about three years of age to about 13 years of age in humans); adolescent (e.g., from about 13 years of age to about 18 years of age in humans), young adult (e.g., front about 18 years of age to about 35 years of age in humans), adult (from about 35 years of age to about 55 years of age in humans) or elderly (e.g., from about 55 years and beyond of age in humans).

In many embodiments, cells are labeled by contacting the cells wish an emulsion of the imaging reagent, such that the reagent is taken up by cells. Both phagocytic and non-phagocytic cells may be labeled by such a method. For example, as demonstrated in WO2005072780, both dendritic cells (phagocytic) and gliosarcoma cells (non-phagocytic) can be labeled by contacting the cells with an emulsion of the imaging reagent.

It certain aspects, a method of the invention may comprise labeling cells in vivo with a $^{19}$F imaging reagent and detecting labeled cells in the subject. The cells to be labeled may be determined by specific properties of the cells such as phagocytic activity. The cells that are labeled may be controlled by the route of administration of the imaging reagent. The types of cells that are labeled may be controlled by the nature of the imaging reagent. For example, simple colloidal suspensions of imaging reagent will tend to be taken up more quickly by cells with phagocytic activity. As another example, an imaging reagent may be formulated with or covalently bound to a targeting moiety that facilitates selective targeting of the imaging reagent to a particular population of cells. In certain embodiments, the imaging reagent comprises perfluoro-15-crown ether.

In certain embodiments the cells to be labeled are stem cells. Stem cell therapies are commonly used as part of an ablative regimen for treatment of cancer with high dose radiation and/or chemotherapeutic agents. Ablative regimens generally employ hematopoietic stem cells, or populations of cells containing hematopoietic stem cells, as may be obtained, for example, from peripheral blood, umbilical cord blood or bone marrow. Cells of this type, or a portion thereof, may be labeled and tracked in vivo to monitor survival and engraftment at the appropriate location. Other types of stem cells are increasingly attractive as therapeutic agents for a wide variety of disorders.

As an example, cells may be mouse embryonic stem cells, or ES cells from another model animal. The labeling of such cells may be useful in tracking the fate of such cells administered to mice, optionally as part of a preclinical research program for developing embryonic stem cell therapeutics. Examples of mouse embryonic stem cells include: the JMI ES cell line described in M. Qiu et al., Genes Dev 9, 2523 (1995), and the ROSA line described in G. Friedrich, P. Soriano, Genes Dev 5, 1513 (1991), and mouse ES cells described in U.S. Pat. No. 6,190,910. Many other mouse ES lines are available from Jackson Laboratories (Bar Harbor, Me.). Examples of human embryonic stem cells include those available through the following suppliers; Arcos Bioscience, Inc., Foster City, Calif., CyThera, Inc., San Diego, Calif., BresaGen, Inc., Athens, Ga., ES cell International, Melbourne, Australia, Geron Corporation, Menlo Park, Calif., Göteborg University, Göteborg, Sweden, Karolinska Institute, Stockholm, Sweden, Maria Biotech Co. Ltd.—Maria infertility Hospital Medical Institute, Seoul, Korea, MizMedi Hospital—Seoul National University, Seoul, Korea, National Centre for Biological; Sciences/Tata Institute of Fundamental Research, Bangalore, India, Pochon CHA University, Seoul, Korea, Reliance Life Sciences, Mumbai, India, ReNeuron, Surrey, United Kingdom, StemCells, Inc., Palo Alto, Calif., Technion University, Haifa, Israel, University of California, San Francisco, Calif., and Wisconsin Alumni Research Foundation, Madison, Wis. In addition, examples of embryonic stem cells are described in the following U.S. patents and published patent applications: U.S. Pat. Nos. 6,245,566; 6,200,806; 6,090,622; 9,351,406; 6,090,622; 5,843,780: 20020045259; 20020068045. In preferred embodiments, the human ES cells are selected from the list of approved cell lines provided by the National Institutes of Health and accessible at http://escr.nih.gov. In certain preferred embodiments, an embryonic stem cell line is selected from the group comprising: the WA09 line obtained from Dr. J. Thomson (Univ. of Wisconsin) and the UC01 and UC06 lines, both on the current NIH registry.

In certain embodiments, a stem cell for use in disclosed methods is a stem cell of neural or neuroendocrine origin, such as a stem cell from the central nervous system (see, for example U.S. Pat. Nos. 6,468,794; 6,040,180; 5,753,506; 5,766,948), neural crest (see, for example, U.S. Pat. Nos. 5,589,376; 5,824,489), the olfactory bulb or peripheral neural tissues (see, for example. Published US Patent Applications 20030003579; 10020123143; 20020016002 and Gritti et al. 2002 J Neurosci 22 (2):437-45), the spinal cord (see, for example, U.S. Pat. Nos. 6,361,996, 5,851,832) or a neuroendocrine lineage, such as the adrenal gland, pituitary gland or certain portions of the gut (see, for example, U.S. Pat. No. 6,171,610 and PC12 cells as described in Kimura et al. 1994 J. Biol. Chem. 269: 1896-67). In preferred embodiments, a neural stem cell is obtained from a peripheral tissue or an easily healed tissue, thereby providing art autologous population of cells for transplant.

Hematopoietic or mesenchymal stem cells may be employed in certain disclosed methods. Recent studies suggest that bone marrow-derived hematopoietic (HSCs) and mesenchymal stem cells (MSCs), which are readily isolated, have a broader differentiation potential than previously recognized. Purified HSCs not only give rise to all cells in blood, but can also develop into cells normally derived from endoderm, like hepatocytes (Krause et ah, 2001, Cell 105: 360-77; Lagasse et al., 2000 Nat Med 6: 1229-34). Similarly, HSCs from peripheral blood and from umbilical cord blood are expected to provide a useful spectrum of developmental potential. MSCs appear to be similarly multipotent, producing progeny that can, for example, express neural cell markers (Pittenger et al., 1999 Science 284: 143-7; Zhao et al., 2002 Exp Neurol 174: 11-20). Examples of hematopoietic stem cells include those described in U.S. Pat. Nos. 4,714,680; 5,061,620; 5,437,994; 5,914,108; 5,925,567; 5,703,197; 5,750,397; 5,716,827; 5,643,741; 5,061,620. Examples of mesenchymal stem cells include those described in U.S. Pat. Nos. 5,486,350; 5,327,735, 5,942,235; 5,972,703, those described in PCT publication nos. WO 00/53705, WO 00/02654; WO 98/20907, and those described in Pittenger et. al. and Zhao et al., supra.

Stem cell lines are preferably derived from mammals, such as rodents (e.g. mouse or rat), primates (e.g. monkeys, chimpanzees or humans), pigs, and ruminants (e.g. cows, sheep and goats), and particularly from humans. In certain embodiments, stem cells are derived from an autologous source or an HLA-type matched source. For example, stem cells may be obtained from a subject in need of pancreatic hormone-producing cells (e.g. diabetic patients in need of insulin-producing cells) and cultured to generate autologous insulin-producing cells. Other sources of stem cells are easily obtained from a subject, such as stem cells from muscle tissue, stem cells from skin (dermis or epidermis) and stem cells from fat.

In some preferred embodiments, cells for administration to a human should be compliant with good tissue practice guidelines set by the U.S. Food and Drug Administration (FDA) or equivalent regulatory agency in another country. Methods to develop such a cell line may include donor testing, and avoidance of exposure to non-human cells and products.

Cells derived from a donor (optionally the patient is the donor) may be administered as unfractionated or fractionated cells, as dictated by the purpose of the cells to be delivered. Cells may be fractionated to enrich for certain cell types prior to administration. Methods of fractionation are well known in the art, and generally involve both positive selection (i.e., retention of cells based on a particular property) and negative selection (i.e., elimination of cells based on a particular property). As will be apparent to one of skill in the art, the particular properties (e.g., surface markers) that are used for positive and negative selection will depend on the desired population of cells. Methods used for selection/enrichment of cells may include immunoaffinity technology or density centrifugation methods. Immunoaffinity technology may take a variety of forms, as is well known in the art, but generally utilizes an antibody or antibody derivative in combination with some type of segregation technology. The segregation technology generally results in physical segregation of cells bound by the antibody and cells not bound by the antibody, although in some instances the segregation technology which kills the cells bound by the antibody may be used for negative selection.

Any suitable immunoaffinity technology may be utilized for selection/enrichment of the selected cells to be used, including fluorescence-activated cell sorting (FACS), panning, immunomagnetic separation, immunoaffinity chromatography, antibody-mediated complement fixation, immunotoxin, density gradient segregation, and the like. After processing in the immunoaffinity process, the desired cells (the cells bound by the immunoaffinity reagent in the case of positive selection, and cells not bound by the immunoaffinity reagent in the case of negative selection) are collected and either subjected to further rounds of immunoaffinity selection/enrichment, or reserved for administration to the patient.

Immunoaffinity selection/enrichment is typically carried out by incubating a preparation of cells comprising the desired cell type with an antibody or antibody-derived affinity reagent (e.g., an antibody specific for a given surface marker), then utilizing the bound affinity reagent to select either for or against the cells to which the antibody is bound. The selection process generally involves a physical separation, such as can be accomplished by directing droplets containing single cells into different containers depending on the presence or absence of bound affinity reagent (FACS), by utilizing an antibody bound (directly or indirectly) to a solid phase substrate (panning, inmmnoaffinity chromatography), or by utilizing a magnetic field to collect the cells which are bound to magnetic droplets via the affinity reagent (immunomagnetic separation). Alternately, undesirable cells may be eliminated from the preparation using an affinity reagent which directs a cytotoxic insult to the cells bound by the affinity reagent. The cytotoxic insult may be activated by the affinity reagent (e.g., complement fixation), or may be localized to the target cells by the affinity reagent (e.g., immunotoxin, such as ricin B chain).

Although it is expected that methods disclosed herein will be frequently used for in vivo monitoring of cells, it should be noted that the methodologies are equally effective for the monitoring of cells in culture, in a tissue sample or other ex vivo cellular material. For therapeutic uses, cells may be labeled at a desired step during the preparation for administration to the patient.

A variety of methods may be used to label cells with imaging reagent. In general, cells will be placed in contact with imaging reagent such that the imaging reagent becomes associated with the cell. Conditions will often be standard cell culture conditions designed to maintain, cell viability. The term "associated" is intended to encompass any manner by which the imaging reagent and cell remain in sufficiently close physical proximity for a sufficient amount of time as to allow the imaging reagent to provide useful information about the position of the cell, whether in vivo or in vitro. Imaging reagent may be located intracellularly, e.g. after phagocytosis or surfactant mediated entry into the cell. Immune cells, such as dendritic cells, macrophages and T cells are often highly phagocytic and data presented herein and in other studies demonstrate that such cells, and other phagocytic cell types, are readily labeled. Other cell types, such as stem cells may also be labeled, regardless of phagocytic activity. Imaging reagent may be inserted into a cell membrane or covalently or non-covalently bound to an extracellular component of the cell. For example, certain linear fluorocarbons described herein may be derivatized to attach one or more targeting moiety. A targeting moiety will be selected to facilitate association of the imaging reagent with the cell to be labeled. A targeting moiety may be designed to cause non-specific insertion of the fibrocarbon into a cell membrane (e.g., a hydrophobic amino acid sequence or other hydrophobic moiety such as a palmitoyl moiety or myristoyl moiety) or to facilitate non-specific entry into the cell. A targeting moiety may bind to a cell surface component, as in the case of receptor ligands. A targeting moiety may be a member of a specific binding pair, where the partner is a cell surface component. The targeting moiety may be, for example, a ligand for a receptor, or an antibody, such as a monoclonal or polyclonal antibody or any of the various polypeptide binding agents comprising a variable portion of an immunoglobulin (e.g., Fv fragment, single chain Fv (scFv) fragment, Fab' fragment, F(ab')2 fragment, single domain antibody, camelized antibody, humanized antibody, diabodies, tribodies, tetrabodies). In certain embodiments, the fluorocarbon imaging reagent comprises perfluoro-15-crown ether.

Cellular labeling with fluorocarbons emulsions can also be facilitated using transfection agents to aid in cell delivery. Often transfection agents consist of cationic lipids, cationic liposomes, poly-cations, and the like. The transfection agent is pre-mixed with the fluorocarbon emulsion labeling agent, whereby it becomes associated with, or coats, the emulsion droplets. The transfection agent-treated emulsion droplets are then added to the cultured cells and incubated so that the cells become labeled. Common transaction agents include Lipofectamine (Invitrogen, Inc) FuGene, DOTAP (Roche Diagnostics, Inc.), and poly-L-lysine. Small proteins can also be used as transfection agents, such as many types of protamines. Protamines, the major DNA-landing proteins in the nucleus of sperm in most vertebrates, package the DNA in a volume less than 5% of a somatic cell nucleus. Protamines are simple proteins of low molecular weight that are rich in arginine and strongly basic. Commercially available protamines come from the sperm of salmon and certain other species of fish. The term "protamine" as used herein, refers to a low molecular weight cationic, arginine-rich polypeptide. The protamine molecule typically comprises about 20 to about 200 amino acids and is generally characterized by containing at least 20%, 50% or 70% arginine. Protamines are often formulated as salts, with one or more counter ions such as sulfate, phosphate and chloride.

Data provided in this application show that protamines (e.g., protamine sulfate) are highly effective in delivering PFPE fluorocarbon emulsion droplets to cultured cells. Suitable protamine sulfates can come from a variety of sources (e.g., salmon, herring, trout, etc.) and be of various grades and forms (e.g., USP, grades II, III, X, etc.), with and without histones or any recombinant derivative. Examples of other protamine solutions that may be used as transfection agents include protamine phosphate, protamine chloride, protamine sulfate-2, protamine sulfate-3, protamine sulfate-10, and protamine free base.

Data provided in this application shows self deliverable nanoemulsions prepared with fluorocarbon imaging reagents (e.g., perfluoro-15-crown-5 ether or PFPE oxide) and incorporate a Plutonic™ surfactant, optionally with Protamine Sulfate, or Cremophor® EL with an emulsifier and an additive. Simple co-incubation of cells with certain self-deliverable nanoemulsions provides sufficient cell labeling for imaging, without the need for transfection reagents.

Where cells are to be used in a therapeutic regimen, various methods have been used for delivery of cells including injections and use of special devices to implant cells in various organs. The present invention is not tied to any particular delivery method. Labeled cells may be monitored regardless of whether the cells are delivered directly to a particular site or delivered systemically. For example, labeled DCs were successfully imaged following either a focal implantation directly into tissues or an intravenous injection, and T-cells were imaged following intraperitoneal injection. Cells may be inserted into a delivery device which facilitates introduction by injection or implantation into the subjects. Such delivery devices may include tubes, e.g., catheters, for injecting cells and fluids into the body of a recipient subject. In a preferred embodiment, the tubes additionally have a needle, e.g., a syringe, through which the cells of the disclosure can be introduced into the subject at a desired location. The cells may be prepared for delivery in a variety of different forms. For example, the cells may be suspended in a solution or gel or embedded in a support matrix when contained in such a delivery device. Cells may be mixed with a pharmaceutically acceptable carrier or diluent in which the cells of the disclosure remain viable. Pharmaceutically acceptable carriers and diluents include saline, aqueous buffer solutions, solvents and/or dispersion media. The use of such earners and diluents is well known in the art. The solution is preferably sterile and fluid. Preferably, the solution is stable under the conditions of manufacture and storage and preserved against the contaminating action of microorganisms such as bacteria and fungi through the use of, for example, parabens, chlorobutanol, phenol, ascorbic acid, thimerosal, and the like. Solutions of the disclosure may be prepared by Incorporating cells as described herein in a pharmaceutically acceptable carrier or diluent and, as required, other ingredients enumerated above, followed by filtered sterilization.

4. Nuclear Magnetic resonance Techniques

As described herein, nuclear magnetic resonance techniques may be used to detect populations of labeled cells. The term "detect" is used to include any effort to ascertain the presence or absence of a labeled molecule or cell, particularly by a nuclear magnetic resonance technique. The term "detect" is also intended to include more sophisticated measurements, including quantitative measurements and two- or three-dimensional image generation. For example, MRI may be used to generate images of such cells. In many instances, the labeled cells may be administered to a living subject. Following administration of the cells, some portion of the subject, or the entire subject, may be examined by MRI to generate an MRI data set. In other instances, the emulsion is injected directly iv, and the subject is subsequently imaged at one or more time points. A "data set", as the term is used herein, is intended to include raw data gathered during magnetic resonance probing of the subject material, the acquisition parameters, as well as information processed, transformed or extracted from the raw data. The raw data includes transient signals obtained by MRI/MRS, including the free-induction decays, spin-echoes, stimulated-echoes, and/or gradient echoes. Examples of processed information include two-dimensional or three-dimensional pictorial representations of the subject material. The processed information may also include magnitude images, the real and imaginary image components, as well as the associated phase map images. Another example of extracted information is a score representing the amount or concentration of imaging reagent or $^{19}F$ signal in the subject material. By using the amount of $^{19}F$ signal in the subject material, and a calibration of the mean amount of imaging reagent per cell pre-implantation (m the case of ex vivo labeling), one can estimate the absolute number of cells in the subject material. The amount of $^{19}F$ signal present in a subject material can be represented or calculated in many ways; for example, the average signal-to-noise-ratio (SNR) of the $^{19}F$ signal for a region of interest (ROI) may be measured and used to calculate the abundance of labeled cells. In certain embodiments, the average intensity, or pixel- or voxel-wise summation of the $^{19}F$ signal may be used to calculate the abundance of labeled cells. This type of data may be gathered at a single region of the subject, such as, for example, the spleen or another organ of particular relevance to the labeled cells. Labeled cells may be examined in contexts other than in the subject. It may be desirable to examine labeled cells in culture. In certain embodiments, labeled cells may be applied to or generated within a tissue sample or tissue culture, and labeled cells may therefore be imaged in those contexts as well. For example, an organ, tissue or other cellular material to be transplanted may be contacted with an imaging reagent to generate labeled cells prior to implantation of such transplant in a subject.

In general, labeling agents of the disclosure are designed for use in conventional MRI detection systems. In the most common implementation of MRI, one observes the hydrogen nucleus (proton, $^{1}H$) in molecules of mobile water contained in subject materials. To detect labels disclosed herein, an alternate nucleus is detected, $^{19}F$. $^{19}F$ MRI has only slightly less intrinsic sensitivity compared to $^{1}H$; the relative sensitivity is approximately 0.83. Both have a nuclear spin of $+\frac{1}{2}$. The natural isotopic abundance of $^{19}F$ is 100%, which is comparable to 99.985% for $^{1}H$. The physical principles behind the detection and image formation are the same for both $^{1}H$ and $^{19}F$ MRI. The subject material is placed in a large static magnetic field. The field tends to align the magnetic moment associated with the $^{1}H$ or $^{19}F$ nuclei along the field direction. The nuclei are perturbed from equilibrium by pulsed radio-frequency (RF) radiation at the Larmor frequency, which is a characteristic frequency proportional to the magnetic field strength where nuclei resonantly absorb energy. Upon removing the RF, the nuclei induce a transient voltage in a receiver antenna; this transient voltage constitutes the nuclear magnetic resonance (NMR) signal. Spatial information is encoded in both the frequency and/or phase of the NMR signal by selective application of magnetic field gradients that are superimposed onto the large static field. The transient voltages are generally digitized, and then these signals may be processed by, for example, using a computer to yield images.

At constant magnetic field strength, the Larmor frequency of $^{19}F$ is only slightly lower (~6%) compared to $^{1}H$. Thus, it is straightforward to adapt conventional MRI scanners, both hardware and software, to acquire $^{19}F$ data. The $^{19}F$ detection may be coupled with different types of magnetic resonance scans, such as MRI, MRS or other techniques. Typically, it will be desirable to obtain a $^{1}H$ MRI image to compare against the $^{19}F$ image. In a living organism or other biological tissue, the proton MRI will provide an image of the subject material and allow one to define the anatomical context of the labeled cells detected in the $^{19}F$ image. In a preferred embodiment of the disclosure, data is collected for both $^{19}F$ and $^{1}H$ during the same session; the subject is not moved during these acquisitions to better ensure that the two data sets are in spatial registration. Normally, $^{19}F$ and $^{1}H$ data sets are acquired sequentially, in either order. An RF coil (i.e. antenna) can be constructed that can be electrically tuned from the $^{19}F$ and $^{1}H$ Larmor frequency. Tuning between these two frequencies can be performed manually (e.g. via an electro-mechanical variable capacitor or inductor), or electrically, via active electronic circuitry. Alternatively, with appropriate modifications to the hardware and/or software of the MRI instrument, both data sets can be acquired simultaneously, for example, to conserve imaging time. Simultaneous acquisition of the $^{19}F$ and $^{1}H$ data sets require an RF coil or antenna that can be electrically tuned simultaneously to the $^{19}$F and $^1$H Larmor frequency (i.e., a double-tuned coil). Alternatively the RF coil can be "broadband," with one broadly-tuned electrical resonance that covers both Larmor frequencies (i.e. $^{19}$F and $^1$H). Other imaging techniques, such as fluorescence detection may be coupled with $^{19}$F MRI. This will be particularly desirable where a fluorocarbon imaging reagent has been derivatized with a fluorescent moiety. In other embodiments, the $^{19}$F MRI scan may be combined with a PET scan in the same subject or patient by using dual-model radioactive $^{18}$F/$^{19}$F fluorocarbon labeling reagents as described herein.

MRI examination may be conducted according to any suitable methodology known in the art. Many different types of MRI pulse sequences, or the set of instructions used by the MRI apparatus to orchestrate data collection, and signal processing techniques (e.g. Fourier transform and projection reconstruction) have been developed over the years for collecting and processing image data (for example, see *Magnetic Resonance Imaging, Third Edition*, editors D. D. Stark and W. G. Bradley, Mosby, Inc., St. Louis Mo. 1999). The reagents and methods of this disclosure are not tied to any particular imaging pulse sequence or processing method of the raw NMR signals. For example, MRI methods that can be applied to this disclosure broadly encompasses spin-echo, stimulated-echo, gradient-echo, free-induction decay based imaging, and any combination thereof. Fast imaging techniques, where more than one line in k-space or large segments of k-space are acquired from each excited signal, are also highly suitable to acquire the $^{19}$F (or $^1$H) data. Examples of fast imaging techniques include fast spin-echo approaches (e.g. FSE, turbo SE, TSE, RARE, or HASTE), echo-planar imaging (EPI), combined gradient-echo and spin-echo techniques (e.g. GRASE), spiral imaging, and burst imaging. The development of new and improved pulse sequence and signal processing methods is a continuously evolving field, and persons skilled in the art can devise multiple ways to image the $^{19}$F labeled cells in their anatomical context.

As another example of a nuclear magnetic resonance technique, MRS can be used to detect the presence of fluorocarbon-labeled cells in localised tissues or organs. Normally MRS methods are implemented on a conventional MRI scanner. Often the localized volume of interest (VOI) is defined within a conventional anatomical $^1$H MRI scan. Subsequently, the magnitude of the $^{19}$F NMR signal observed within the VOI is directly related to the number Of labeled cells, and/or the mean concentration of PFPE per cell present in the tissue or organ. Methods for isolating a VOI within a much larger subject are well known the art (for example, *Magnetic Resonance Imaging, Third Edition*, Chapter 9, Editors D. D. Stark and W. G. Bradley, Mosby, Inc., St Louis Mo. 1999). Examples include using a localised RF surface coil near the VOI, surface spoiling, surface coil $B_1$-gradient methods, slice-selective $B_0$-gradient techniques, STEAM, PRESS, image selective in vivo spectroscopy (ISIS), and magnetic resonance spectroscopic imaging (MRSI). The development of new and improved pulse sequence and signal processing methods is continuously evolving for MRS, and persons skilled in the art can devise multiple ways to detect the $^{19}$F NMR signals emanating from the fluorocarbon labeled cells in VOIs.

In certain cases the subject material is a fixed or otherwise preserved specimen of tissue that has been biopsied or necropsied from the animal or human. The subject material is then subjected to conventional high-resolution, one or multi-dimensional, liquid state $^{19}$F NMR to determine the amount of fluorine present in the sample. The fluorine content is directly related to the number of labeled cells in the subject material specimen. In the case of in situ labeling of resident phagocytes (e.g., monocytes, macrophage, neutrophil, cells of the liver) with fluorine emulsion as described above (e.g., using nanoemulsion 3), the amount of $^{19}$F measured in the sample is directly proportional to the number of these phagocytes present in the tissue. In this way one can assay the relative amount of inflammation in the intact tissues without having so use histology or any other destructive and time-consuming techniques. In certain embodiments, to analyze the $^{19}$F content of the tissue, one uses one-dimension $^{19}$F NMR. In certain embodiments, a $^{19}$F reference compound will be added to the sample of known number of $^{19}$F spins that has a chemical shift that is different than the composition of the cell labeling emulsion (see below). In certain embodiments, the relative integrated areas under the emulsion peak and reference peak can be used to calculate the absolute number of fluorines present in the tissue sample. In certain embodiments, the weight of the tissue sample can also be incorporated into the calculation to extract the mean fluorine density of the tissue sample, and this parameter can be considered a quantitative index of inflammation or "inflammation Index".

In certain embodiments the disclosure provides a method of quantifying the numbers of labeled cells in vivo or in subject materials within an ROI. An ROI may include all labeled cells in a subject or labeled cells in specific organs such as the pancreas, specific tissues such as lymph nodes, or any region or of one or more voxels showing detectable MRI/MRS $^{19}$F signal. A ROI can be an otherwise undefined area beyond a particular experiment. There are a number of ways that labeled cells may be quantified in the subject materials or in vivo, as described herein.

In the case or ex vivo labeling, calibrating the mean "cellular dose" of $^{19}$F labeling agent pre-implantation of a particular cell population is often a pre-requisite for quantitative cell determinations in subject materials or the patient. It is anticipated that different cell types have different inmate abilities to take up the labeling agents in vitro, and thus the cellular dose of the labeling agent will also vary. Furthermore, different cells of the same type acquired from different sources (e.g., different patients) may have different affinities for the labeling agent. Thus a cellular dose calibration may be required. This calibration may be used, initially, to modify the labeling protocol (i.e., incubation conditions, duration of time that cells are incubated with labeling fluorocarbon emulsion, concentration of fluorocarbon emulsion in culture medium during labeling, etc.) to achieve a certain range of cellular dose before labeled cells are actually used in a subject to be imaged. Alternatively, one can fix the labeling conditions and protocol and measure the mean value $^{19}$F labeled per cell, as is, for subsequent quantification in the subject to be imaged. In certain embodiments the mean number of $^{19}$F molecules (F's) per cell of a labeled cell population is measured (i.e., calibrated) in vitro prior to administration of the cells to the subject or patient. In certain embodiments the mean number of $^{19}$F molecules (F's) per cell of a labeled cell population is calibrated in a test population of cells of a particular type, not necessarily destined for a patient, but used to calibrate cellular dose of labeling agent as a consequence of a particular labeling protocol or set of conditions; optionally, the value of cellular dose is then used for future labeling and in vivo imaging experiments in the same population type of cells with the same labeling protocol.

The cellular dose of labeling agent can be assayed in vitro using a variety of quantitative techniques. For example, one can use a one-dimensional (1D) $^{19}$F NMR spectrum obtained from a cell pellet, cell suspension, or cell lysate, of a known number of labeled cells. From this spectrum, one can calculate the integrated area of the $^{19}$F spectrum or a portion thereof, originating from the labeling reagent associated with the cells. The integrated area of the $^{19}$F spectrum, denoted $S_{cells}$, is directly proportional to the total amount of $^{19}$F in the cell pellet, suspension, or lysate. To measure the absolute number of $^{19}$F nuclei, the measured $S_{cells}$ may be normalized to a $^{19}$F standard. A $^{19}$F standard can be, for example, a solution of a known volume and concentration of a fluorochemical, where one can calculate the total number of $^{19}$F nuclei in the standard, denoted $F_{scan}$. A suitable fluorochemical reference ideally has a simple $^{19}$F NMR spectrum, preferable with a single narrow resonance (e.g. trifluoroacetic acid or TFA) and optionally a $^{19}$F chemical shift that is significantly different than the labeling fluorocarbon. The $^{19}$F standard can be placed in the same NMR tube as the labeled cell material being measured, in a separate tube, or optionally can be measured in a separate experiment using the same NMR instrument. The integrated area of the spectrum from the $^{19}$F standard, denoted $S_{scan}$, can then be measured. Subsequently, the mean number of $^{19}$F per labeled cell, denoted $F_c$, can be calculated, for example using the formula:

$$F_e = \frac{S_{cells}}{S_{x\,tan}} F_{s\,tan} \frac{1}{N_{cells}}$$

where $N_{cells}$ is the number of labeled cells contained in the in vitro test sample. Quantitative NMR methods for $^{19}$F and other nuclei are well know in the art, and those skilled can devise many variations to the cellular dose calibration procedure described above. Besides $^{19}$F NMR, there are other quantitative methods that can be used to assay the cellular dose of the labeling reagent. For example, a reagent may be labeled fluorescently, luminescently, optically, or radioactively (see US Patent Application No. 2007-0258886, herein incorporated by reference in its entirety).

Similarly, in the case of in situ cell labeling of circulating phagocytes following iv injection of emulsion, to measure the effective cell labeling, one can extravesate a portion of peripheral blood from the subject and measure the effective cell loading of leukocytes using the methods described above. Furthermore, one or more of the various cell sorting or enrichment techniques can be used to sort out phagocytic cells (e.g., macrophages) prior to the loading measurement (above) to better define which cell population has been labeled in situ. The measured cell labeling parameter can then be used to calculate the apparent number of inflammatory cells present in tissue using the magnetic resonance methods described herein.

In order to extract accurate quantification of labeled cells and/or relative inflammation score from the $^{19}$F MRI/MRS data sets, additional calibrations and standards may be employed. For example, one can use a calibrated external $^{19}$F reference (i.e., phantom) during the actual $^{19}$F MRI/MRS scan of the subject material containing labeled cells. The image intensity of the calibrated phantom is used, tor examples, when analyzing the $^{19}$F MRI/MRS data set to proved an absolute standard for the number of $^{19}$F nuclei when examining the subject material or patient. The calibrated phantom is used to normalise the sensitivity of the particular MRI/MRS system that has been loaded with a particular subject to be imaged. The $^{19}$F reference may be, for example, one or more vessels containing a solution of a known concentration of $^{19}$F nuclei. In preferred embodiments, the solution contains a dilute concentration of the emulsified fluorocarbon labeling reagent. Optionally, the solution contains non-emulsified fluorocarbon labeling reagent, a gel, or liquid, for example that has been diluted in a suitable solvent. Optionally, the solution can be composed of another fluoro-chemical, ideally wish a simple $^{19}$F NMR spectrum, preferable with a single narrow NMR resonance (e.g. trifluoroacetic acid (TFA) or trifluoroacetamide (TFM) and other fluorinated acids, trifluorotoluene or trifluoroethanol). In preferred embodiments, the T1 and T2 values of the reference solution are similar to those of the labeling reagent. Optionally, the solution can contain perfluorocarbon-labeled cells, or lysines of the same. The non-cellular reference has the advantage of longer storage times. Optionally, the solution can take the form of a gel. The vessel containing the solution is preferably sealable, and can take a variety of geometries; preferred vessel geometries include ellipsoidal, cylindrical, spherical, and parallel piped shapes. One or more vessels containing $^{19}$F reference solution can be used during the $^{19}$F MRI/MRS of the subject material if multiple $^{19}$F references (i.e. vessels) are used they can contain the same $^{19}$F concentration or different concentrations, and in the case of the latter, they ideally contain graded concentrations of fluorochemical. The placement of the calibrated $^{19}$F reference vessel(s) can be placed preferably externally or alongside, or optionally inside, the imaged subject or patient prior to data acquisition. In preferred embodiments, the reference is imaged using $^{19}$F MRI along with the subject in the same image field of view (FOV). Optionally, $^{19}$F MRS data is acquired in the reference either sequentially or in parallel with the subject data set. Optionally, data from the reference can be acquired using MRI/MRS acquired in a separate scan. Optionally, the external reference is not scanned along with a subject in every $^{19}$F MRI/MRS examination, but rather, values of the reference $^{19}$F signal intensity acquired using MRI/MRS is used from a scan of a comparable subject or a simulated-subject. In a given $^{19}$F MRI/MRS scan, the calibrated $^{19}$F standard may be sampled by one or more voxels. The observable $^{19}$F intensity produced by a voxel may be proportional to the concentration of the fluorochemical in the solution (or gel) and the voxel volume. Often in a $^{19}$F MRI scan the reference standard is comprised of many voxels. Often one calculates the mean intensity of one, several, or all voxels in the reference standard. Optionally, the mean image intensity is calculated over an ROI defined with in the $^{19}$F image of the reference standard. Optionally, the physical geometry of the reference standard vessel contributes to defining the observed $^{19}$F signal intensity, for example, the volume compartment(s) containing the $^{19}$F reference solution is smaller than the voxel volume. In other embodiments, the calibrated external reference relies on a solution with a $^{1}$H signal intensity of a known number of detectable $^{1}$H; in this case the sensitivity of the $^{19}$F signal in the subject material is reference to a $^{1}$H calibrated standard. Ideally the solution or gel in the $^{1}$H calibrated reference (contained in a vessel as described above) yields a simple $^{1}$H NMR spectrum, preferable with a single narrow NMR resonance (e.g., $H_2O$, or mixtures of $H_2O$—$D_2O$). Other than a different nuclei, the use of the $^{1}$H standard reference is the same in many other respects as described above for the $^{19}$F reference. Optionally, the calibrated reference standard contains any other MRI/MRS-active nuclei. In some embodiment, the reference is an internal organ or tissue detected via $^{1}$H MRI/MRS, where the data may be raw or normalized. In other embodiments, the reference is a standard that is not scanned with the subject, but is calibrated by relevant factors such as the weight of the patient or the size of the body cavity.

By computationally manipulating or combining two or more key parameters from the $^{19}$F MRI/MRS data set, one can calculate the number of labeled cells and/or relative amount of inflammation present in an ROI as described herein. For example, a fey set of parameters may include: (i) the cellular dose of labeling agent (i.e., $F_c$) measured in vitro; (ii) in vivo $^{19}$F MRI/MRS data set taken in the subject at one or more time points following labeled cell administration; (iii) the voxel volume; (iv) the in-plane voxel area (i.e., area of the image pixel); (v) optionally, the MRI/MRS data set from the $^{19}$F reference standard; (vi) optionally, the measured Johnson noise of the $^{19}$F MRI/MRS data in the subject material; (vii) optionally, the measured signal-to-noise ratio (SNR) of one or more voxels of the $^{19}$F MRI/MRS data set in the subject material; (viii) optionally, the measured SNR of one or more voxels of the $^{19}$F MRI/MRS data set from the reference standard; (ix) optionally, the $^{19}$F NMR relaxation times (T1, T2, and T2*) of the subject material; (x) optionally, the $^{19}$F NMR relaxation times (T1, T2, and T2*) of the reference standard (for example, see *Magnetic Resonance Imaging, Third Edition*, chapter 4, editors D. D. Stark and W. G. Bradley, Mosby, Inc., St, Louis Mo. 1999). Those skilled in the art can derive other parameters, combinations of the above set, or derivations thereof, particularly from the $^{19}$MRI/MRS dataset, that can be used to quantify the number of labeled cells in situ. In certain embodiments the above set of key parameters can be used to derive quantitative or statistical measures of the accuracy or confidence of the measured number of labeled cells.

There are many ways to combine the key parameters, (i-x, above), any subsets of these, or any of their combinations or approximations, to estimate the effective number of labeled cells seen by $^{19}$F MRI in the subject material, denoted by $N_c$. For example, one can use an equation of the form $$N_c = \frac{[F_R]v}{I_R} \frac{1}{F_e} \sum_{i=1}^{N_{ROI}} I_c^{(i)}$$

where: $N_c$=total number of labeled cells in the ROI; $[F_R]$=concentration of $^{19}$F in the calibrated $^{19}$F reference solution (or gel); v=voxel volume; $I_R$=mean intensify of the calibrated $^{19}$F reference taken with the MRI/MRS scan, averaged over one or more voxels, $F_c$=average $^{19}$F cellular dose of the labeling agent measured in vitro; $N_{ROI}$=number of voxels in the ROI containing labeled cells; $I_c^{(i)}$=image intensify of the $i^{th}$ voxel in the ROI containing labeled cells; i=unitless index for voxels in the ROI containing labeled cells.

There are also many ways to approximate $N_c$ from the $^{19}$F data set. For example, one could use the expression $$N_c \approx \frac{I_c^{avg}}{I_R} [F_R] v \frac{1}{F_e} N_{ROI}$$

where $I_c^{avg}$ is the average intensity of the ROI containing the labeled cells, (i.e. the average intensity of the $N_{ROI}$ voxels). As another example, one could use $$N_c \approx \frac{I_c^{avg}}{I_R} V_e \frac{1}{F_e} [F_R]$$

where $V_c$ is the total volume of the ROI containing the labeled cells. As a further example, one could use $$N_c \approx \frac{I_c^{avg}}{I_R} \frac{V_c}{V_R} \frac{1}{F_e} N_R$$

where $V_R$ is the effective volume of the reference in the $^{19}$F MRI/MRS and $N_R$ is the number $^{19}$F nuclei in $V_R$. Note that in all of the above formulas the various intensities (i.e., $I_R$, $I_c^{avg}$, $I_c^{(i)}$) can be normalized to the image noise, and thus the above formulas can be equivalently expressed in terms of the appropriate SNR values for the particular regions. Thus, there are many ways to estimate the number of labeled cells, $N_c$, and many similar forms of these basic expressions can be derived by basic mathematical manipulations, however, all rely on the same basic content contained within the input parameters described by (i-x). Furthermore, quantification of labeled cells in an ROI need not be expressed in terms of absolute numbers or effective cell numbers. Other quantitative indices can be derived that are indicative of the amount of cells in an ROI. For example, one can calculate the ratio $I_c^{avg}/I_R$, or the ratio of the average SNR values observed in the ROI and the reference; all of these fall within subsets of the above expressions and/or the parameters.

It is noted that the above analysis of cell numbers and related indices assume that the $^{19}$F NMR relaxation times (i.e., particularly T1 and/or T2) of the fluorocarbon label is approximately the same as material in the calibrated $^{19}$F reference standard. In the case that the relaxation times are not comparable, one of skill in the art can readily correct for this by employing the known MRI intensity equations of the particular imaging protocol being used, expressed in terms of T1 and T2.

Optionally, the $^{19}$F MRI data set of the subject material can undergo post-processing before the actual cell quantification calculation is performed (as described above). For example, post-processing algorithms may include "de-noising" the $^{19}$F data set. This can be accomplished by, for example, by thresholding the image to cut off low-intensity noise; this involves rescaling the image intensity so that low values are set to zero. In magnitude MRI images, random Johnson noise is often apparent and uniformly distributed across the image FOV. It is well know in the art that one can threshold out the low-level image intensity so that regions known to contain no true signal (i.e. devoid of $^{19}$F and/or $^1$H nuclei) appear to have a null or very near-null intensity. This process can be performed in an ad-hoc fashion (i.e., "manually" or by visual inspection), or by using a computer algorithm. In other embodiments, de-noising of the data set can be achieved by using other algorithms, for example using wavelet analysis, and many methods are known in the art for image de-noising. The following references are incorporated in their entirety herein: Khare, A., et al., INTERNATIONAL JOURNAL OF WAVELETS MULTIRESOLUTION AND INFORMATION PROCESSING, 3 (4): 477-406 December 2005; Cruz-Enriquez, H., et al., IMAGE ANALYSIS AND RECOGNITION, 3656: 247-254 2005; Awate, S P., et al., INFORMATION PROCESSING IN MEDICAL IMAGING PROCEEDINGS, 3565: 677-688 7005; Ganesan. R.; et al., IIE TRANSACTIONS, 36 (9): 787-806 September 2004; Seheunders, P., IEEE TRANSACTIONS ON IMAGE PROCESSING, 13 (4): 475-485 April 2004; Ghugre, N R., MAGNETIC RESONANCE IMAGING, 21 (8): 913-921 October 2003; Bao, P., et al., IEEE TRANSACTIONS ON MEDICAL IMAGING, 22 (9): 1089-1099 September 2003; Wu, Z Q., et al., ELECTRONICS LETTERS, 39 (7): 603-605 Apr. 3, 2003; LaConte, S M., et al., MAGNETIC RESONANCE IN MEDICINE, 44 (5): 746-757 November 2000: Laine, A F., ANNUAL REVIEW OF BIOMEDICAL ENGINEERING, 2: 511-550 2000; Zuroubi, S., et al., MAGNETIC RESONANCE IMAGING, 18 (1): 59-68 January 2000: Nowak, R D., IEEE TRANSACTIONS ON IMAGE PROCESSING, 8 (10): 1408-1419 October 1999; and Healy, D M., et al., ANNALS OF BIOMEDICAL ENGINEERING, 23 (5): 637-665 SEP-OCT 1995.

Other types of post-processing algorithms are know in the art that can be applied to the $^{19}$F MRI data set before or after quantification, such as zero-filing (A Handbook of Nuclear Magnetic Resonance, $2^{nd}$ Edition, Ray Freeman, Addison Wesley Longman Press 1997) and various image interpolation, de-noising, and image smoothing algorithms (for example, see The Image Processing Handbook, $3^{rd}$ Edition, John C. Russ, CRC Press/IEEE Press).

In certain embodiments the above set of key parameters (i-x) can be used to derive quantitative or statistical measures of the accuracy or confidence of the measured number of labeled cells or related indices. $^{19}$F MRI/MRS data sets are often subject to SNR limitations within ROI, and thus if is often useful to calculate a metric of the confidence or accuracy of the measurement. Many methods are known in the art for the statistical analysis of MRI and other biomedical-type images. The claimed embodiment is understood to encompass these known methods.

5. Pharmaceutical Formulations and Uses

Methods of administration of the emulsions of the application are well-known to those of skill in the art. To achieve the desired activity, the emulsions can be administered in a variety of unit dosage forms. The dose will vary according to the particular emulsion. The dose will also vary depending on the manner of administration, the overall health, condition, size, and age of the patient.

In certain embodiments, administration of the emulsions may be performed by an intravascular route, e.g., via intravenous infusion by injection. In certain embodiments, other routes of administration may be used. Formulations suitable for injection are found in Remington's Pharmaceutical Sciences, Mack Publishing Company, Philadelphia, Pa., 17th ed. (1983). Such formulations must be sterile and non-pyrogenic, and generally will include a pharmaceutically effective carrier, such as saline, buffered (e.g., phosphate buffered) saline, Hank's solution, Ringer's solution, dextrose/saline, glucose solutions, and the like. The formulations may contain pharmaceutically acceptable auxiliary substances as required, such as, tonicity adjusting agents, wetting agents, bactericidal agents, preservatives, stabilizers, and the like. In certain embodiments suitable buffers for intravenous administration are used to aid in emulsion stability. In certain embodiments glycols are used to aid in emulsion stability.

In certain embodiments, administration of the emulsions may be performed by a parenteral route, typically via injection such as intra-articular or intravascular injection (e.g., intravenous infusion) or intramuscular injection. Other routes of administration, e.g., oral (p.o.), may be used if desired and practicable for the particular emulsion to be administered.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the pharmaceutical compositions of the application.

In certain embodiments, formulations of the subject emulsions are pyrogen-free formulations which are substantially free of endotoxins and/or related pyrogenic substances. Endotoxins include toxins that are confined inside microorganisms and are released when the microorganisms are broken down or die. Pyrogenic substances also include fever-inducing, thermostable substances (glycoproteins) from the outer membrane of bacteria and other microorganisms. Both of these substances can cause fever, hypotension and shock if administered to humans. Due to the potential harmful effects, it is advantageous to remove even low amounts of endotoxins from intravenously administered pharmaceutical drug solutions. The food & Drug Administration ("FDA") has set an upper limit of 5 endotoxin units (EU) per dose per kilogram body weight in a single one hour period for intravenous drug applications (The United States Pharmacopeial Convention, Pharmacopeial Forum 26 (1):223 (2000)).

Formulations of the subject emulsions include those suitable for oral, dietary, topical, parenteral (e.g., intravenous, intraarterial, intramuscular, subcutaneous injection), ophthalmologic (e.g., topical or intraocular), inhalation (e.g., intrabronchial, intranasal or oral inhalation, intranasal drops), rectal, and/or intravaginal administration. Other suitable methods of administration can also include rechargeable or biodegradable devices and controlled release polymeric devices. Stents, in particular, may be coated with a controlled release polymer mixed with an agent of the application. The pharmaceutical compositions of this disclosure can also be administered as part of a combinatorial therapy with other agents (either in the same formulation or in a separate formulation).

The amount of the formulation which will be therapeutically effective can be determined by standard clinical techniques. In addition, in vitro assays may optionally be employed to help identify optimal dosage ranges. The precise dose to be employed in the formulation will also depend on the route of administration. Effective doses may be extrapolated from dose-response curves derived from in vitro or animal model test systems. The dosage of the compositions to be administered can be determined by the skilled artisan without undue experimentation in conjunction with standard dose-response studies. Relevant circumstances to be considered in making those determinations include the condition or conditions to be treated, the choice of composition to be administered, the age, weight, and response of the individual patient, and the severity of the patient's symptoms. For example, the actual patient body weight may be used to calculate the dose of the formulations in milliliters (mL) to be administered. There may be no downward adjustment to "ideal" weight. In such a situation, an appropriate dose may be calculated by the following formula: Dose (mL)=[patient weight (kg)×dose level (mg/kg)/drug concentration (mg/mL)]

Therapeutics of the disclosure can be administered in a variety of unit dosage forms and their dosages will vary with the size, potency, and in vivo half-life of the particular therapeutic being administered.

For in situ applications, emulsions may be formulated to have optimal pharmacokinetic properties to enable uptake by phagocytes before clearance of the emulsion.

Doses of therapeutics of the disclosure will also vary depending on the manner of administration, the particular use of the emulsion, the overall health, condition, size, and age of the patient, and the judgment of the prescribing physician.

The formulations of the application can be distributed as articles of manufacture comprising packaging material and a pharmaceutical agent which comprises the emulsion and a pharmaceutically acceptable carrier as appropriate to the mode of administration. The pharmaceutical formulations and uses of the disclosure may be combined with any known compositions for the applications of the application.

6. Computer Methods

Methods for quantifying labeled cells will typically be conducted with the aid of a computer, which may operate software designed for the purpose of such quantification. Such software may be a stand-alone program or it may be incorporated into other software, such as MRI image processing software (see US Patent Application No. 2007-0253910, herein incorporated by reference in its entirety).

The disclosure will be more readily understood by reference to the following examples, which are included merely for purposes of illustration, of certain aspects and embodiments of the present application, and are not intended to limit the disclosure.

EXAMPLES

Unless indicated, all of the following presented nanoemulsions are prepared with Perfluoro-15-crown ether, a well known fluorocarbon in the art used for formulating emulsions as blood substitutes, for oxygen sensing and cell tracking (see U.S. Pat. Nos. 4,838,274 and 5,785,950, herein incorporated by reference in their entirety). In following examples we introduced novel approaches to formulate stable nanoemulsions with perfluoro-15-crown 5 ether. Other novel formulations incorporate various co-emulsifiers rendering the emulsions "self-deliverable" into Various cell types. The novel emulsion formulations described herein show marked improvements over prior art emulsions, particularly with respect to a decreased nanoemulsion droplet size (as low as 110 nm), which is advantageous for in vivo applications. Presented nanoemulsions presented are prepared as monodisperse (PDI>0.1) and show exceptional stability in presence of serum and at body temperatures. Further novelty lies in introducing protamine sulfate or other co-surfactants for achieving "self-deliverable" properties and the use of Cremophor EL, for achieving exceptionally small droplet size and high stability in vivo.

All presented nanoemulsions were prepared on 0.5-1 liter scale using microfluidation. The emulsions were analyzed by dynamic light scattering (DLS) for droplet size and polydispersity using a Malvern Zetasizer Nano ZS. The appearance of the emulsions was evaluated visually. The nanoemulsions were tested for serum stability, pH and osmolality. Furthermore, the efficacy for in vivo experiments has been demonstrated.

Serum experiments were all done in DMEM (Dubelco modified essential media, Invitrogen Inc.) media in the presence of 10% FBS (Fetal bovine serum, Hyclone Inc.).
Abbreviations
w/w weight/weight ratio
RT mom temperature
PDI polydispersity index
WFI water for injection (sterile)
PSA droplet size analysis
MF Microfluidizer
Material
Perfluoro-15-crown-5-ether: ExFluor, Inc. Round Rock, Tex.
Protamine sulfate; Sigma P3369 lot no022K12201 CAS# 53597-25-4 Meets USP testing
Pluronic F68: BASF (Lutrol F68/Poloxamer 188) USP/NF grade
Water for injection: Braun (sterile/pyrogene free)
Cholesterol: Sigma Cholesterol Ph Eur: 14606
DFPE: Dipalmitoyl phosphatidylethanol from Avanti Polar Lipids: 16:0 PE 850705P
Lecithin (Egg PC): Lipoid Egg Phosphatidyl Choline
Cremophor ELP: BASF 10205104 USF/NF grade
Propylene glycol: Fagron BV 176947 Ph Eur grade
Perfluoro-15-crown 5 Ether With and Without Protamine Sulfate

TABLE 1

Nanoemulsions 1 and 2 composition with emulsion final volume of 1 L in WFI as external phase.

| Formulation | perfluoro-15-crown-5-ether % w/w | Emulsifier 1 % w/w | Emulsifier 2 % w/w |
|---|---|---|---|
| 1 | 15% | 0.6% Pluronic F68 | |
| 2 | 15% | 0.6% Pluronic F68 | 0.04% Protamine Sulphate |

Procedure:

A highly concentrated pro-emulsion was prepared first, diluted with sterile water to reach needed final concentration and finally processed by MF to obtain an emulsion with an acceptable droplet size (<200 nm) and polydispersity (<0.15). Emulsifiers and additives were dissolved in sterile water right before use. Pluronic F68 solution was prepared in water at 100 mg/ml and protamine sulfate at 20 mg/mL. The concentrated pre-emulsion was prepared by processing all the required liquids (perfluoro-15-crown 5 ether oil, F68 solution and Protamine Sulfate solution) with rotary shear (using an ultra-turrax shaft with a diameter of 25 mm) at 13500 rpm for 2.5 minutes. This first mixture was then diluted to the final needed concentration and reprocessed with rotary shear for 1 minute. The pre-emulsions were immediately processed by MF, using an M-110S microfluidizer (Microfluidics Corp.). The liquid pressure during microfluidization processing was >18500 psi, and the low droplet size was achieved by 5 to 8 discrete passes (cycles). The nanoemulsion was sterilized by filtration. The product was filtered using a 47 mm PFR (PTFE, 0.22 µm) disc in a filter holder (PALL, Inc.). Successful filtration was achieved using low flow of 2-8 ml/min.

Emulsions were visually inspected and subjected to droplet size and polydispersity measurements by DLS. All samples were diluted with WFI to reach final concentration of 1% perfluoro-15-crown-5-ether prior to DLS measurements.
Results

TABLE 2

PSA results and visual inspection.

| Formulation | Diameter (nm) | (PDI) | Mean Peak (nm) | Visual Appearance |
|---|---|---|---|---|
| 1 | 149 | 0.036 | 157 | turbid, milky, homogenous |
| 2 | 150 | 0.036 | 158 | turbid, milky, homogenous |

In both formulations, the droplet size was <200 nm and polydispersity <0.2 for 3 months upon storage at 5° C. and room temperature.
Perfluoro-15-crown 5 Ether Nanoemulsion With Cremophor-EL (Formulation 3)

A new formulation of perfluoro-15-crown-5-ether was designed for increased stability and decreased droplet size over currently known lipid based nanoemulsions. This new formulation utilizes for the first time Cremophor® EL (BASF) as an emulsifier for a fluorocarbon. Cremophor EL is a non-ionic solubilizer where the main component of is glycerol-polyethylene glycol ricinoleate, which, together with fatty acid esters of polyethyleneglycol, represents the hydrophobic part; the smaller, hydrophilic component consists of polyethylene glycols and ethoxylated glycerol. The lipid component incorporates into the liposomal coat of the nanoemulsion droplet, while the PEG secures sterile stabilisation. The resulting nanoemulsion droplet has a perfluoro-15-crown-5-ether core, a liposomal coating, and a sterically stabilized surface via the PEG portion of Cremophor EL. Steric stabilization improved markedly shelf life and nanoemulsion stability in vivo. To demonstrate the improvements achieved by introducing Cremophore EL into the emulsion formulation, the prior art formulation (emulsion 4) was prepared following a previously repotted procedure (WO2006096409) side-by-side with the new formulation (emulsion 3). The two emulsions were compared, and the results are presented below. Both emulsions were prepared on a 250 mL scale.

TABLE 3

Emulsions compositions with medium of WFI and liposomes which consisted of 70 mol % lecithin, 28 mol % cholesterol, and 2 mol % DPPE.

| Formulation | perfluoro-15-crown-5-ether % w/v | Emulsifier 1 % w/v | Emulsifier 2 % w/v | Additive % w/v |
|---|---|---|---|---|
| 3 | 35.6% | 3.0% Cremophor ELP | 2.0% Liposomes | 2.0% Propylene Glycol |
| 4 | 35.6% | 2.0% Safflower oil | 2.0% Liposomes | 1.7% Glycerin |

Procedure:

In summary, liposomes were prepared by sonification of the liposomal components. A concentrated pre-emulsion was prepared by adding perfluoro-15-crown-5-ether/emulsifier 1 and additive; subsequently the batch was diluted with water for injection to the final concentration and processed using the MF to the final oil droplet size.

In more detail, the liposomal components lecithin, cholesterol and DPPE were dissolved in chloroform and dried by rotary evaporation into a film. The lipids were then dispersed in WFI by sonication. The resulting suspensions were flushed with argon (gas), closed and stored protected from light at 5° C. until use. All components, including Cremophor® EL (or safflower oil), perfluoro-15-crown-5-ether, propylene glycol, and liposomes were first combined with small amount of water. This initial concentrated mixture had perfluoro-15-crown-5-ether at 60% w/w. The mixture was processed by rotary sheer (turrax) for two minutes at 12500 rpm, and the resulting concentrated pre-emulsion further diluted with WFI to the final volume of and processed again for 1 minute al 12500 rpm. The pre-emulsion was not stable and thus was immediately processed by microfluidization with 5 to 8 discreet passes (cycles) in the MF with a pressure of >18500 psi. The final emulsion product was stable as described below.

Figure 7:
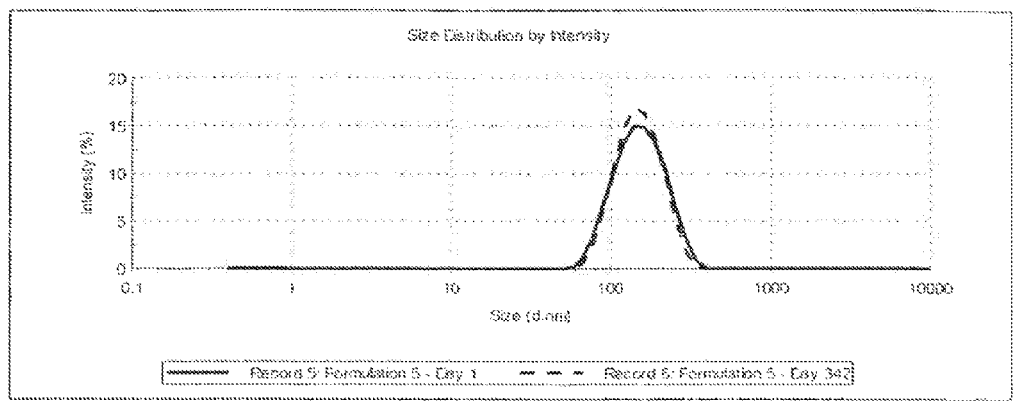
FIG. 7 shows the mean droplet size of nanoemulsion 5 at day 1 and day 342 after formulation (solid and dashed lines, respectively). Data demonstrates the long-term stability, small particle size and narrow particle distribution of nanoemulsion 5.

Formulation 5 was prepared using, the procedure as described above for formulation 3, wherein perfluoro-15-crown-5 ether was replaced by weight with linear PFPE. This replacement was feasible due to similar specific weight and viscosity between the linear PFPE and perfluoro-15-crown-5 ether. The amount of PFPE oxide in formulation 5 was equivalent to weight amount of perfluoro-15-crown 5 ether in formulation 3, with the advantage of obtaining a larger number of equivalent 19F spins/nanoemulsion droplet. The surfactant comixture, Cremophor EL and additive amounts were the same as those described for formulation 3. Briefly, Cremophor® EL (or safflower oil), linear PFPE, propylene glycol, and liposomes were first combined with a small amount of wafer. This initial concentrated mixture comprised linear PFPE at 60% w/w. The mixture was processed by rotary sheer (turrax) for two minutes at 1250 rpm, and the resulting concentrated pre-emulsion was further diluted with WFI to the final volume and processed again for 1 minute at 12500 rpm. The pre-emulsion was stable and was immediately processed by microfluidization with 5 to 8 discreet passes (cycles) in the MF with a pressure of >18500 psi. FIG. 7 shows droplet size measurements by DLS for formulation 5 at day 1 and day 342. These data demonstrated the exceptional stability of this formulation upon storage at 4° C.

Results:

Shelf Life Stability of Formulation 3 Emulsion:

Emulsion 3 was followed by DLS and visually inspected for signs of destabilization for a total of >6 months. A summary of the stability data for formulation 3 is shown in FIG. 1. Formulation 3 appeared upon visual inspection as turbid and milky; no large droplets, aggregates, sedimentation, or phase separation was observed during the follow up. Importantly, the droplet size of the formulation 3 emulsion was smaller as compared to all other emulsions tested, and most importantly the droplet size and PDI were dramatically decreased as compared to formulation 4 (WO2006098499). Comparative results are shown in Table 4. Introduction of Cremophor EL dramatically decreased the droplet size in formulation 3, as compared to formulation 4 prepared with safflower oil under the same manufacturing conditions.

TABLE 4

Comparative droplet size and PDI measurements of Formulations 3 and 4

| Formulation | Diameter (nm) | PDI | Mean Peak (nm) |
|---|---|---|---|
| 3 | 105 | 0.108 | 116 |
| 4 | 217 | 0.053 | 233 |

At both 5° C. and 25° C., a small increase in droplet sue (17% at 5° C. after 2 months and up to 32% at 23° C.) was initially detected. The small increase in droplet size indicated possible Ostwald ripening during the first 2 months of follow up. At time point of 3 months the size stabilized at approximately 150 nm and the PDI remained low (<0.15). The swelling of droplets stopped and the nanoemulsion did not change in its visual appearance and remained stable during the further follow up. Emulsion 3 was tested in presence of serum at two time points, time 0 and at 6 months. At each time point the nanoemulsion droplet size and PDI did not show significant change in presence of serum after 3 h incubation at 37° C. (Table 6).

TABLE 5

Visual appearance, pH and osmolality of Formulation 3.

| Formulation | pH | Osmolality (mOsmol/kg) | Visual Appearance |
|---|---|---|---|
| 3 | 4.7 | 311 | Sample was turbid and milky, no droplets or sedimentation was observed |

TABLE 6

Serum stability of Formulation 3.

| Formulation | Time point/ Conditions | Diameter (nm) | PDI | Mean Peak (nm) |
|---|---|---|---|---|
| 3 | T = 0 week | 105 | 0.108 | 116 |
| 3 in serum | T = 1 hour/ 37° C. | 105 | 0.187 | 129 |
| 3 in serum | T = 3 hour/ 37° C. | 118 | 0.255 | 143 |

Formulation 4 with safflower oil was prepared in parallel with the formulation 3 using previously reported methods (WO2006096499). The droplet size, PDI and serum stability of this emulsion was compared to the formulation 3, which utilizes Cremophor EL (above). The droplet size of formulation 4 was substantially larger than compared to the formulations 1, 2, or 3 (Tables 4 and 7). Droplet size increased approximately 25% after only one week at 5° C. (Table 7). After a 2-week period the apparent plateau value for the droplet size was reached (Table 7). Polydispersity increased considerably, which was not observed in the other formulations. Table 8 shows the serum stability of formulation 4.

TABLE 7

Droplet size and PDI measurements of safflower oil Formulation 4.

| Formulation | Time point/ Conditions | Diameter (nm) | PDI | Mean Peak (nm) |
|---|---|---|---|---|
| 4 | T = 0 | 217 | 0.053 | 233 |
| | T = 1 week/at 5° C. | 229 | 0.158 | 254 |
| | T = 2 week/at 5° C. | 232 | 0.147 | 271 |
| | T = 1 week/at 25° C. | 224 | 0.106 | 252 |
| | T = 2 week/at 25° C. | 229 | 0.132 | 266 |

TABLE 8

Serum stability of Formulation 4 incorporating safflower oil.

| Formulation | Time point/ Conditions | Diameter (nm) | PDI | Mean Peak (nm) |
|---|---|---|---|---|
| 4 | T = 0 week | 217 | 0.053 | 233 |
| 4 in serum | T = 1 hour/ 37° C. | 241 | 0.147 | 282 |
| 4 in serum | T = 3 hour/ 37° C. | 244 | 0.139 | 281 |

Shelf Life Stability of Formulation 5 Emulsion:

The emulsion of formulation 5 was followed by DLS and visually inspected for signs of destabilization for a total of 11 months. As described above, FIG. 7 shows that the particle size and PDI remain unchanged after 342 days (>11 months) upon storage at 4-8° C.

Fluorescent Dye Incorporation in Formulation 3

Figure 2:
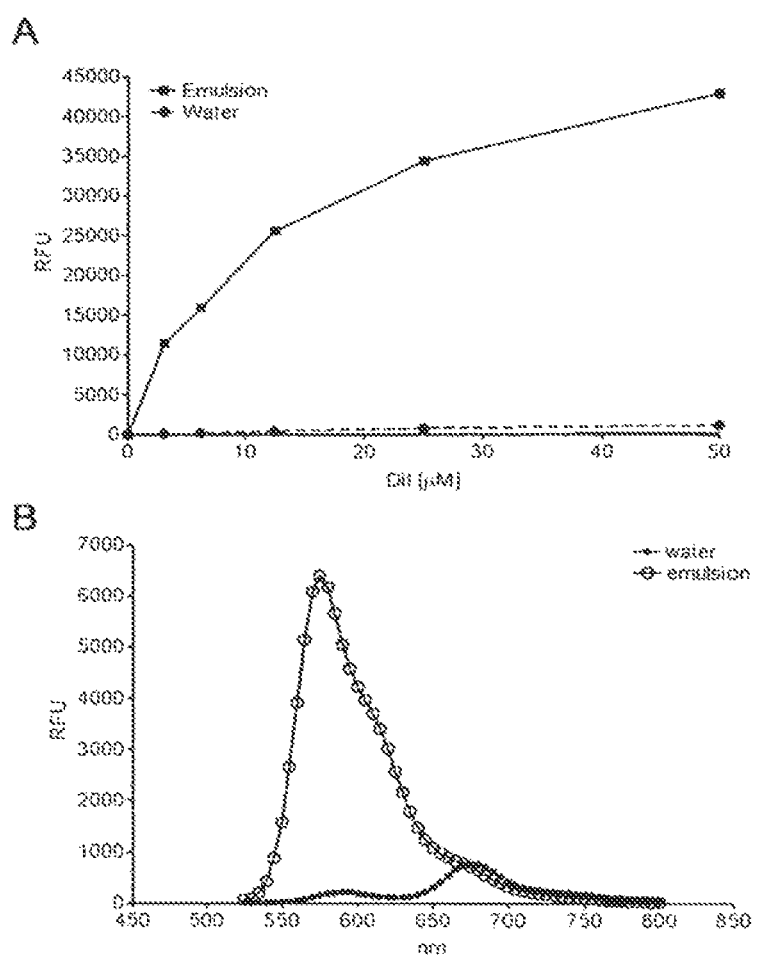
FIG. 2 shows data collected from labeling nanoemulsion 3 with fluorescent dye. A) Fluorescence intensity dependence on dye concentration both in water and bound to emulsion was measured. B) Fluorescence emission spectra of DiI in water and bound to emulsion was obtained.
Figure 3:
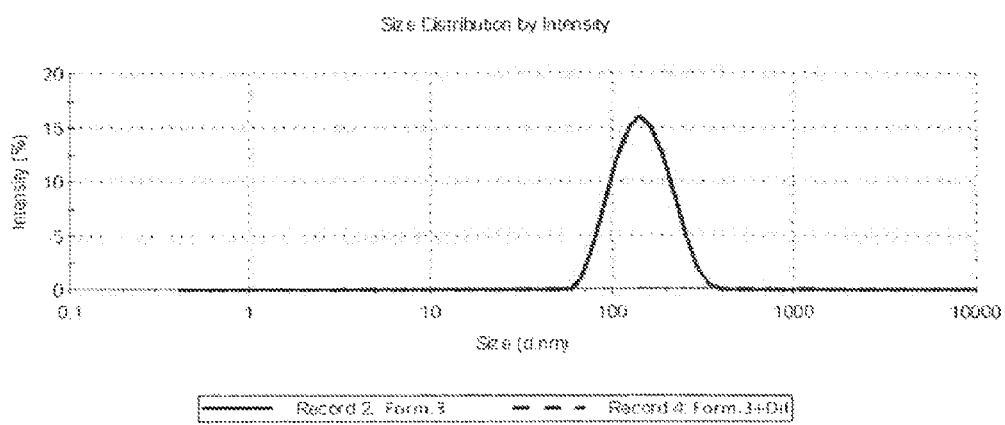
FIG. 3 shows a droplet size comparison of nanoemulsion 3 labeled with fluorescent dye DiI (dashed) and unlabeled (solid).

In order to further demonstrate the usefulness of formulation 3, a fluorescent dye was incorporated into lipid layer of the formulation 3 post-processing. This addition created a 'dual-modality' agent that can be detected both by $^{19}$F magnetic resonance and various fluorescence methods (e.g., flow cytometry, histology, FACs analysis, fluorescence microscopy and the like). Lipophilic dyes that are widely available commercially (e.g., dialkylcarbocyanines, Invitrogen, Inc.) were used. For example, DiI (Molecular Probes), a fluorescent dye that is not soluble in water and shows virtually no fluorescence unless in a lipid, hydrophobic environment, was used. The DiI was incorporated into the liposomal coating of formulation 3. Fluorescence studies showed stable fluorescence of the dye within the liposomal portion of the formulation (FIG. 2). The dye was clearly non-fluorescent unless associated with the emulsion lipid core. Due to low water solubility, the dye remained associated with the nanoemulsion and sustained its fluorescence upon dilution in water or cell culture media. Fluorescent dye incorporation did not affect the droplet size or polydispersity and it did not affect the serum stability of formulation 3, as shown in FIG. 3. The dye also had no negative effects on the nanoemulsion uptake in cells (data not shown).

Formulations 3 and 5 with Protamine Sulfate and Polyethylamine

Nanoemulsions 3 and 5 may also be formulated With protamine sulfate and polyethylamine to improve uptake in non-phagocitic cells. These polyamines are incorporated into the pre-emulsion and integrated into the emulsion surfactant layer following MF processing, as described above. The amount of polyamine will be optimized to achieve optimal cell labeling. (See WO2009/009105, herein incorporated by reference in its entirety).

Formulations 3 and 5 Supplemented with Fluorescent PFPEs

Fluorescent blended PFPE amides (FBPAs) have been recently described that contained covalently conjugated fluorescent dyes (e.g. BODIPyTR, FITC or Alexa647). These fluorescent conjugated PFPE oils behave as unique single fluorocarbon phase during nanoemulsion processing [for details see Janjic et al, J Am Chem Soc. 2008 Mar. 5; 130 (9):2832-41, herein incorporated by reference in its entirety]. Fluorescent versions of the formulations 3 and 5 may be prepared with FBPAs. In formulation 3, 10% v/v of the perfluoro-15-crown-5 ether can be replaced by FBPA. Consequently, in formulation 5, 10% v/v of PFPE oxide is replaced by FBPA. The oils are carefully blended together to obtain unique fluorocarbon phase, and then subjected to nanoemulsion preparation procedures as described for formulation 3 and formulation 5. The advantage of fluorocarbon phase being labeled with fluorescent dye rather then the surfactant co-mixture is multifold. First, the fluorescent dye in these new formulations remains within the fluorocarbon core of the nanoemulsion droplet throughout the processing, during cell labeling, and presumably in vivo. Second, the fluorescent signal is directly proportional to the $^{19}$F NMR signal from the labeled tissue or cells [Janjic et al, J Am Chem Soc. 2008 Mar. 5; 130 (9):2832-41], thus there is no differential labeling between cells (or tissues) for the two imaging or detection modalities (i.e., magnetic resonance and fluorescence).

Biological Evaluation of Formulation 3.

Formulation 3 showed excellent stability and a very small droplet sixe (<150 nm) with low polydispersity (<0.15), as shown in FIG. 1. The nanoemulsion is stable both in vitro, under cell culturing conditions, and in vivo, upon injection to rodents. Here we present more detailed evaluation of the formulation 3, including cellular uptake, toxicity profile, and evaluation of labeled cells for phenotype and activity changes.

Figure 4:
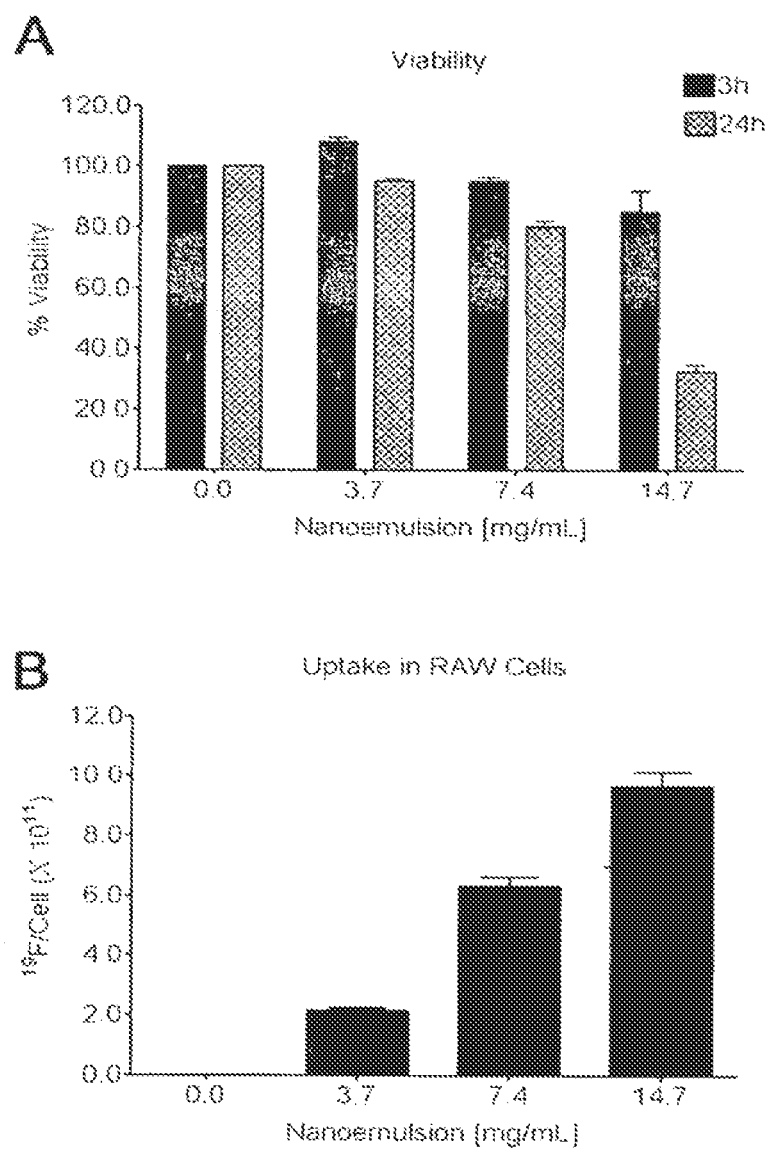
FIG. 4 shows nanoemulsion 3 cytotoxicity and uptake in RAW cells. A) Cells were exposed to different doses of nanoemulsion 3 for 3 and 24 h, and cell viability was assessed by cell counts. B) Uptake in pelleted RAW cells by $^{19}$F NMR after 18 h esposure was measured. Data represent the mean of n=3 cell pellets, and the error bars are ±SD.
Figure 5:
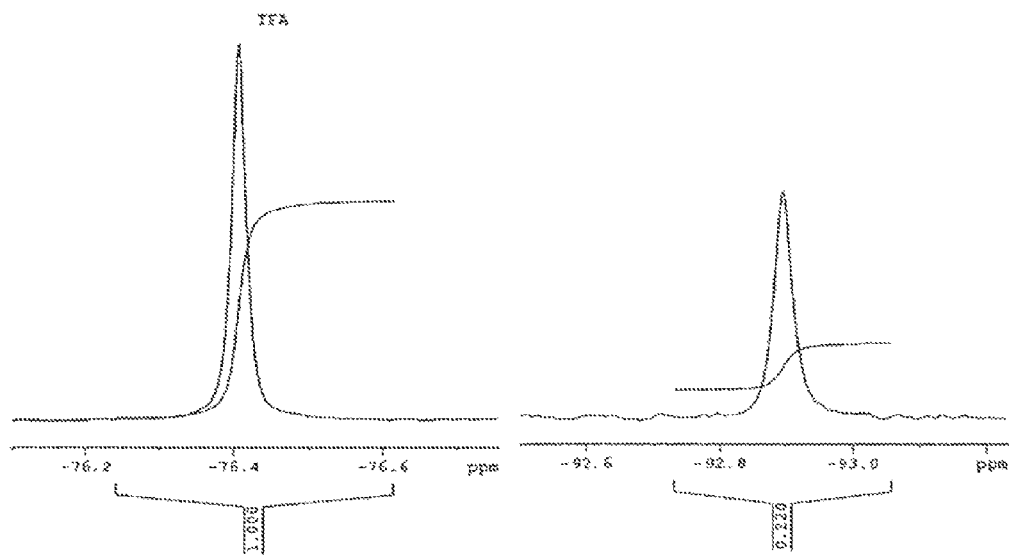
FIG. 5 shows a representative $^{19}$F NMR spectrum of formulation 3 labeled RAW cells. Trifluoroacetic acid was used as an internal standard with chemical shift at −76.00 ppm, while labeled cells show at −92.90 ppm.

RAW cells (ATCC, Manassass, Va.), cultured according to the vendor's instructions, were exposed to different concentrations of formulation 3 for 3 and 24 h, and the cytotoxicity was estimated by direct cell counts. Minimal toxicity was observed at the highest dose applied and after 24 h exposure (FIG. 4A). Formulation 3 uptake in RAW cells was measured by $^{19}$F NMR in cell pellets as describe above and showed clear dose dependence (FIG. 4B). FIG. 5 shows a representative $^{19}$F NMR spectrum of formulation 3 labeled RAW cells. Satisfactory uptake in phagocytic RAW cells was obtained after 18 h co-incubation and without transfection reagents. In order to promote uptake in non-phagocitic cells, protamine sulfate and polyethylamine were incorporated into formulation 3 as described in formulation 2 (above).

Figure 6:
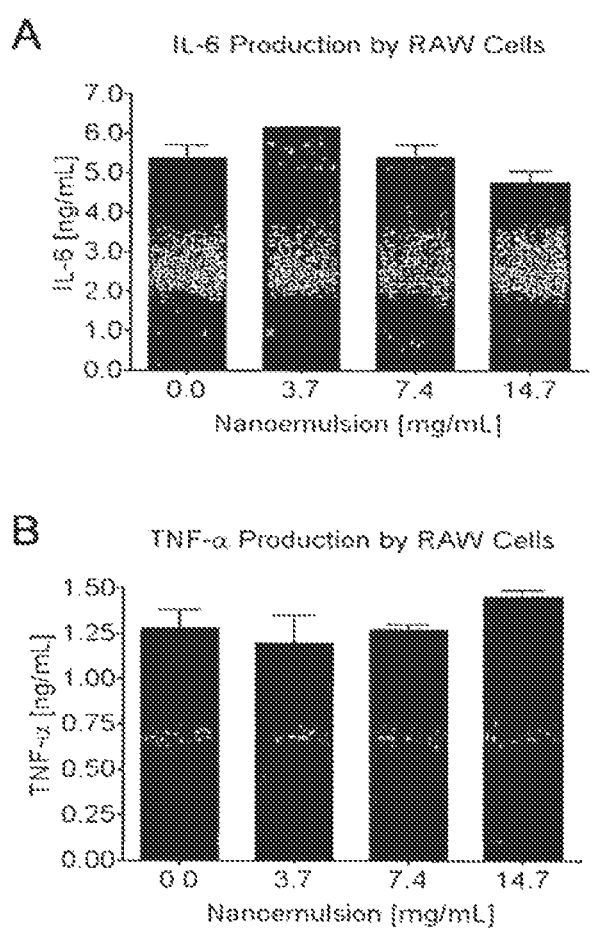
FIG. 6 shows cytokine production in formulation 3 labeled RAW cells. Raw cells labeled with formulation 3 were plated (1×10$^6$ cells/ml) and exposed to 250 ng/ml of LPS. Culture supernatants were collected after 24 h and tested for the presence of IL-6 and TNF-alpha. Cytokine measurements were determined by ELISA. Data are the average of two independent experiments and shown as the mean ±SD.

Formulation 3 cell labeling showed no impact on the cytokine producing capacity of RAW cells (FIG. 6). The cells were activated by LPS for 24 h prior to being exposed to formulation 3 for 18 h, washed, and then cultured for 24 h. An ELISA assay was used to measure cytokine production, including the levels of IL-6 and TNF-alpha. These tests showed that cells labeled with formulation 3 had no impact on their activity in vitro.

Figure 8:
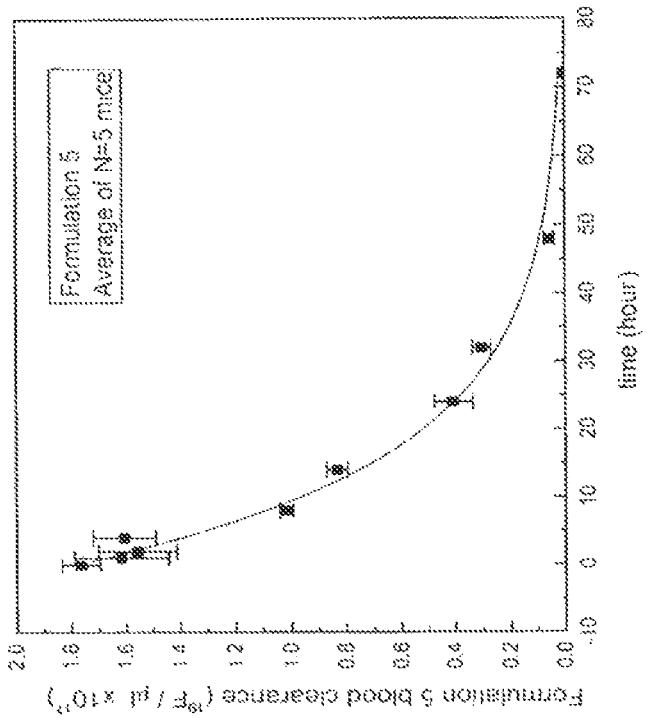
FIG. 8 shows the blood clearance time of intravenously injected formulation 3 and 5 in mouse. The two formulations have a comparable blood half-life. Averaged data were measured using $^{19}$F NMR of serial blood samples take at discrete time points post-injection from a cohort of animals (n=5)
Figure 8:
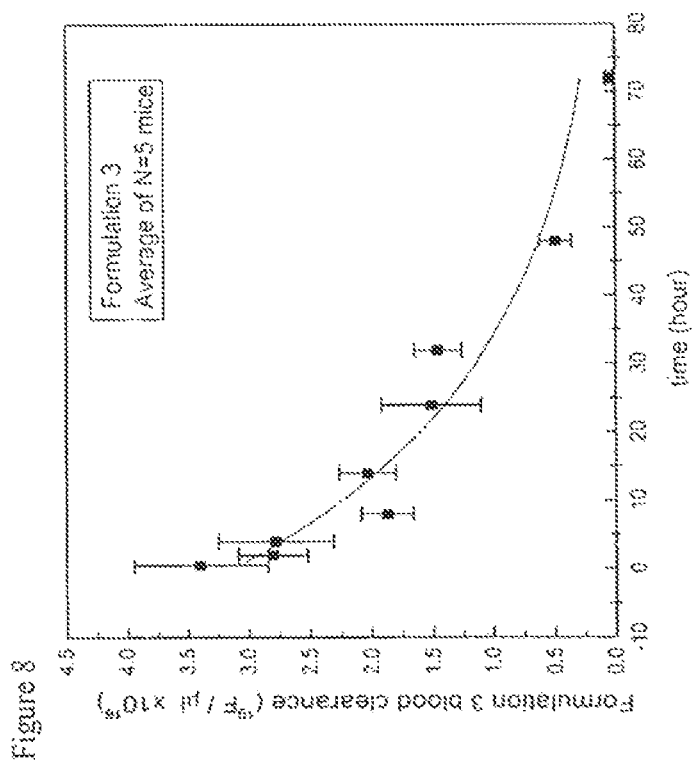

The in vivo blood clearance time was measured for formulations 3 and 5 in rodents (FIG. 8). A cohort of C57BL/6 mice (female, 6 weeks old) were injected with a single 0.5 mL bolus of a given formulation via the tail vein. Upon injection, no adverse effects were observed in these animals. Small alloquots of blood were then sampled from each animal at a fixed set of time points. A sample size of N=5 mice for each formulation was used. The $^{19}$F content of each blood sample was assayed using $^{19}$F NMR; a known volume of each of the blood samples was spiked with a calibrated fluorine reference solution (TFA) as described above, placed in a capillary and the amount of $^{19}$F per blood volume was calculated over time (FIG. 8). Overall, both formulations 3 and 5 had a similarly-long blood half-life (>14 hours, FIG. 8).

Overall, several of the formulations described above (e.g., formulation 3 and 5) were developed to accelerate the routine task of inflammation quantification in intact tissue specimens. In the case of in situ labeling experiments, inflammation can be assayed in two ways—by using conventional high-resolution NMR or by using MRI. In both methods, one detects the abundance of $^{19}$F nuclei in tissue, contained within phagocytic inflammatory cells (e.g., monocyte/macrophage/neutrophil). Most standard NMR instrumentation can routinely detect $^{19}$F. NMR provides a sensitive and cost-effective approach for quantifying the degree of leukocyte infiltration in tissue samples. This approach abrogates the need for time-intensive pathological staining and subsequent cellular quantification via microscopy. No special tissue preparation is required, except for an optional fixation step. Additionally, the use of NMR eliminates the potential for histological sampling bias and error, resulting in smaller, higher quality data sets, NMR analysis of excised tissues is non-destructive, and thus the same tissues may undergo conventional histological or biochemical analysis following NMR.

Figure 9:
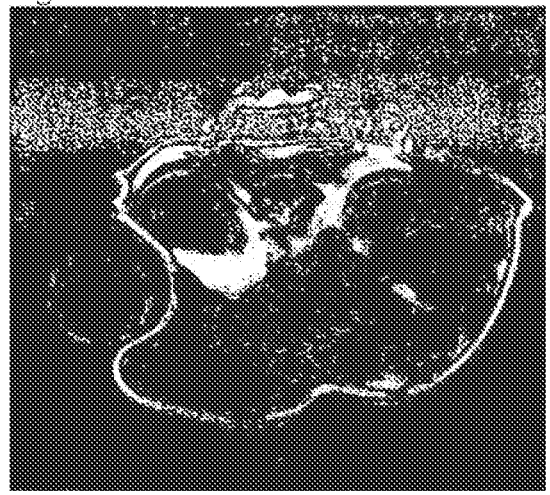
FIG. 9 shows a typical in vivo $^{19}$F/$^1$H MRI data in an inflammation model using nanoemulsion 3. The $^{19}$F data (pseudo-color) shows a highly idealized accumulation of inflammatory Freud's surrounding a surgically implanted sponge soaked in Complete Freud's adjuvant prior to implantation. The $^1$H image (grayscale) provides the anatomical background in this anesthetized mouse.

As a typical example application of the in vivo efficacy of these emulsions, formulation 3 was used to detect inflammation in a sponge granuloma model using in vivo MRI. A PVS sponge disk was soaked in Complete Freund's Adjuvant (CFA) and subcutaneously implanted dorsally in a C57BL/6 mouse. A single intravenous injection of formulation 3 (0.5 ml) was given on day 4 post surgery. The anesthetized mouse was imaged on day 5 at 7 T. FIG. 9 shows a $^1$H/$^{19}$F fusion image, with the $^{19}$F rendered in pseudo-color. The data shows an intense concentration of macrophages labeled with formulation 3 surrounding the sponge (asterisk). A small amount of $^{19}$F is also seen in the liver, a major clearance pathway of the formulation (FIG. 9). 'R' is a dilute $^{19}$F reference capillary along the animal's torso. Control animals with the sponge soaked in saline displayed negative $^{19}$F signal after formulation 3 administration. These example data show the high specificity for inflammation of formulation 3.

As a further example of the utility of the formulations described above, formulation 3 was used to measure the inflammation profile in the spinal cord (SC) of a rodent model of multiple sclerosis, experimental allergic encephalomyelitis (EAE). The EAE model was generated in a DA rat using a single subcutaneous inoculation in the tail base consisiting of isogenic spinal cord homogenate mixed with Complete Freund's Adjuvant (CFA). Clinical Stage-2 EAE rats were intravenously injected with formulation 3 (0.5 mL) 48 hours later intact, fixed segments of the SC were assayed for inflammation using conventional $^{19}$F NMR spectroscopy at 470 MHz (FIG. 10). In FIG. 10, the *Inflammation Index* represents the inflammation density of each spinal cord vertebra, calculated as the number $^{19}$F nuclei per tissue weight. Also shown are control animals receiving CFA, but no SC homogenate, showing minimal formula 3 uptake. Data shown are the mean results for n=3 animals. In this example, the total preparation and analysis time per SC was approximately 6 hours, representing approximately an order of magnitude in time-savings compared to conventional histological analyses.

There are many other recent in vivo experimental examples of the utility of formulation 3 and 5. For instance, Klug et al. (Abstract #3172, *Proc In. Soc. Mag. Reson. Med.* 17, 2009, incorporated by reference herein in its entirety) demonstrated that formulation 5 can be used to visualize acute and chronic inflammation in mouse models. These investigators used both C57BL/6mice, prepared with localized ear injections of TNF-α, and apoE$^{-/-}$ mice, a model of atherosclerotic plaques. Following a single intravenous injection of formulation 5, $^{19}$F could be detected by MRI at sites of TNF-α injection in the C57BL/6 mice, and in the apoE$^{-/-}$ mice, $^{19}$F could be detected in the brachiocephatic arch region, which is a common site of plaques in these animals.

In other studies, Hitchens et al (Abstract #932, *Proc. Int. Soc. Mag. Reson. Med.* 17, 2009, incorporated by reference herein in its entirety) uses formulation 3 to visualize solid organ transplant rejection. Either the heart/lung or kidney from a DA rat was transplanted into a BN rat strain. In both cases, the DA to BN transplantation serves as an experimental allograft model that experiences acute rejection. Several days after transplant, a single injection of formulation 3 was delivered to these animals intravenously and then the animals were subjected to $^{19}$F/$^1$H MRI 24 hours later. The in vivo $^{19}$F data clearly showed the infiltration of inflammatory cells into the rejecting organs, but not in controls (non-rejecting) organs. Validating histological studies confirmed that the $^{19}$F signal originates from infiltrating macrophage.

Other investigators (Basse-Lusebrink et al., Abstract #807. *Proc. Int. Soc. Mag. Reson. Med.* 17, 2009, incorporated by reference herein in its entirety) used both formulations 3 and 5 in a mouse model of cortical infarction. Infarcted animals received IP injections of either formulations and a pronounced, localized $^{19}$F MRI signal was observed from presumed macrophage infiltration into the ischemic cortical lesion. The authors further showed that the small (~1 ppm) chemical shift between perfluoro-15-crown-5 ether and the linear PFPE used in formulation 3 and 5, respectively, could be spectroscopically resolved in vivo to reveal emulsions injected at different time points, and thus different waves of inflammatory cells into the lesion. Using conventional spatially-localized chemical shift imaging (CSI) they were able to simultaneously defect and resolve the in vivo brain distribution of both formulations that were injected at different time points.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

Equivalents

While specific embodiments of the subject inventions are explicitly disclosed herein, the above specification is illustrative and not restrictive. Many variations of the inventions will become apparent to those skilled in the art upon review of this specification and the claims below. The full scope of the inventions should be determined by reference to the claims, along with their full scope of equivalents, and the specification, along with such variations.

We claim:

1. An aqueous composition as an nanoemulsion, said composition comprising a fluorine-containing imaging agent, selected from the group consisting of perfluoro-15-crown-5 ether and PFPE oxide, glycerol polyethylene glycol ricinoleate, a surfactant co-mixture, and an additive, wherein said fluorine-containing imaging agent lacks a ligand-targeting moiety, wherein said nanoemulsion has a mean droplet size of less than 200 nm in diameter and a polydispersity index of between 0.1 and 0.2.

2. The aqueous composition of claim 1, wherein the surfactant co-mixture comprises 70 mol % lecithin, 28 mol % cholesterol, and 2 mol % dipalmitoyl phosphatidylethanolamine.

3. The aqueous composition of claim 1, wherein the additive is propylene glycol.

4. An aqueous composition as an nanoemulsion, said composition comprising a fluorine-containing imaging agent, selected from the group consisting of perfluoro-15-crown-5ether and PFPE oxide from about 20% to about 40% w/v, glycerol polyethylene glycol ricinoleate from about 2.0% to about 4.0% w/v, a surfactant co-mixture from about 1.0% to about 3.0% w/v, wherein the surfactant co-mixture comprises lecithin, cholesterol, and dipalmitoyl phosphatidylethanolamine, and an additive in 2.0% w/v, wherein the additive is propylene glycol, wherein said fluorine-containing imaging agent lacks a ligand-targeting moiety, wherein said nanoemulsion has a mean droplet size of less than 200 nm in diameter and a polydispersity index of between 0.1 and 0.2.

* * * * *